(12) United States Patent
Durduran et al.

(10) Patent No.: US 11,705,248 B2
(45) Date of Patent: Jul. 18, 2023

(54) SYSTEM AND COMPUTER-IMPLEMENTED METHOD FOR DETECTING AND CATEGORIZING PATHOLOGIES THROUGH AN ANALYSIS OF PULSATILE BLOOD FLOW

(71) Applicants: FUNDACIO INSTITUT DE CIENCIES FOTONIQUES, Barcelona (ES); INSTITUCIO CATALANA DE RECERCA I ESTUDIS AVANCATS, Barcelona (ES); HEMOPHOTONICS, S.L., Barcelona (ES)

(72) Inventors: Turgut Durduran, Barcelona (ES); Jonas Fischer, Barcelona (ES); Ameer Ghouse, Barcelona (ES); Udo Weigel, Barcelona (ES)

(73) Assignees: FUNDACIO INSTITUT DE CIENCIES FOTONIQUES, Barcelona (ES); INSTITUCIO CATALANA DE RECERCA I ESTUDIS AVANCATS, Barcelona (ES); HEMOPHOTONICS, S.L., Barcelona (ES)

( * ) Notice: Subject to any disclaimer, the term of this patent is extended or adjusted under 35 U.S.C. 154(b) by 797 days.

(21) Appl. No.: 16/567,585

(22) Filed: Sep. 11, 2019

(65) Prior Publication Data
US 2020/0090819 A1    Mar. 19, 2020

(30) Foreign Application Priority Data
Sep. 14, 2018 (EP) .................................. 18382664

(51) Int. Cl.
*G16H 70/60* (2018.01)

(52) U.S. Cl.
CPC .................................. *G16H 70/60* (2018.01)

(58) Field of Classification Search
CPC ....... G16H 70/60; G16H 50/30; G06K 9/0053
See application file for complete search history.

(56) References Cited

U.S. PATENT DOCUMENTS

| 7,547,283 B2 | 6/2009 | Mourad et al. |
| 2006/0009700 A1* | 1/2006 | Brumfield ............ A61B 5/6838 600/587 |

(Continued)

FOREIGN PATENT DOCUMENTS

WO    2016164891 A1    10/2016

OTHER PUBLICATIONS

P. Zakharov, A.C. Völker, M.T. Wyss, F. Haiss, N. Calcinaghi, C. Zunzunegui, A. Buck, F. Scheffold, and B. Weber, "Dynamic laser speckle imaging of cerebral blood flow," Opt. Express 17, 13904-13917 (Year: 2009).*

(Continued)

*Primary Examiner* — Evangeline Barr
(74) *Attorney, Agent, or Firm* — Lucas & Mercanti, LLP

(57) ABSTRACT

System and computer-implemented method for detecting and categorizing pathologies through an analysis of pulsatile blood flow. The method has a pulsatile blood flow signal of a subject, extracting a set of features from the pulsatile blood flow signal; and categorizing a pathology based on the extracted features. The extracted features may be predetermined features or features learned through a machine learning algorithm. For the categorization, a classification or a regression algorithm may be used to provide an index or a value score as a biomarker. Additional static features of the subject may be used in the categorization.

8 Claims, 23 Drawing Sheets

(56) References Cited

U.S. PATENT DOCUMENTS

| | | | |
|---|---|---|---|
| 2006/0063995 A1* | 3/2006 | Yodh | A61B 5/0261 600/323 |
| 2012/0162438 A1* | 6/2012 | Thakor | A61B 5/0075 348/161 |
| 2014/0107433 A1* | 4/2014 | Wegerich | G16H 50/30 600/301 |
| 2018/0103861 A1* | 4/2018 | Sutin | A61B 5/318 |
| 2019/0053745 A1* | 2/2019 | Nakaji | A61B 5/0261 |

OTHER PUBLICATIONS

Ashwin B. Parthasarathy, Erica L. Weber, Lisa M. Richards, Douglas J. Fox, Andrew K. Dunn, "Laser speckle contrast imaging of cerebral blood flow in humans during neurosurgery: a pilot clinical study," J. Biomed. Opt. 15(6) 066030 (Nov. 1, 2010) (Year: 2010).*

* cited by examiner

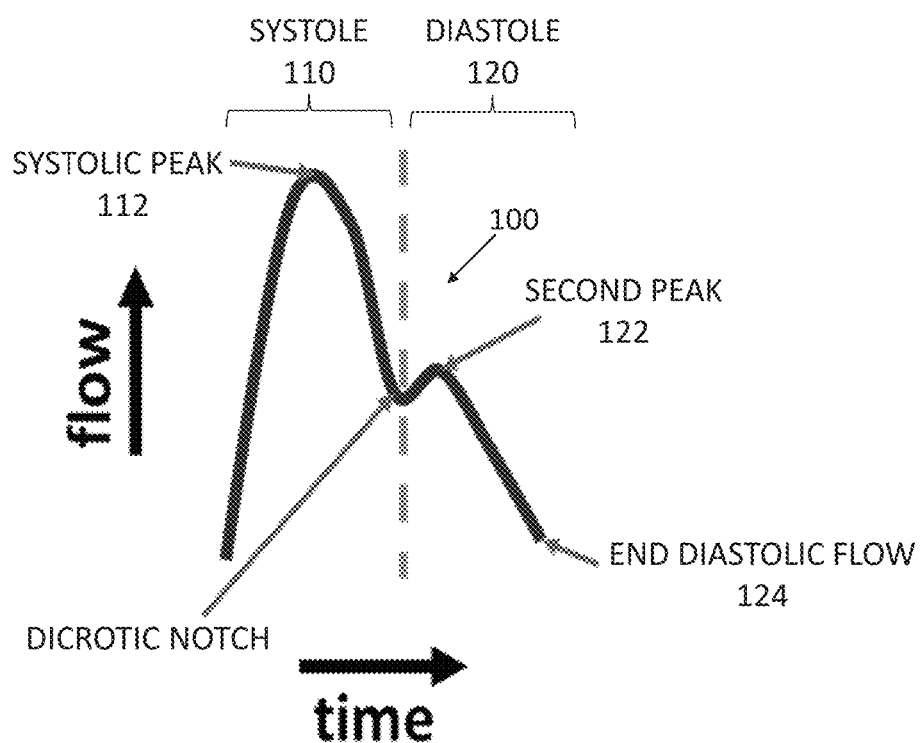
Fig. 1
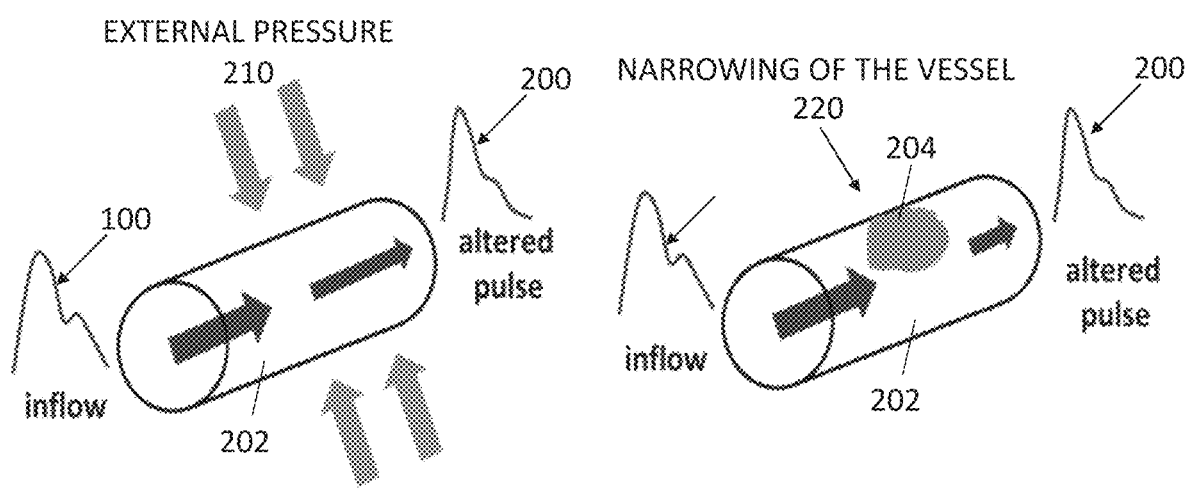
Fig. 2A
Fig. 2B

SYSTEM AND COMPUTER-IMPLEMENTED METHOD FOR DETECTING AND CATEGORIZING PATHOLOGIES THROUGH AN ANALYSIS OF PULSATILE BLOOD FLOW

CROSS-REFERENCE TO RELATED APPLICATIONS

This application claims the benefit of priority from European Patent Application No. 18382664, filed Sep. 14, 2018, the content of which is incorporated herein by reference.

FIELD

The present disclosure is comprised in the field of devices, systems and methods used to detect and categorize pathologies, diseases or situations that cause a change in the pulsatile blood flow of a patient.

BACKGROUND

Some pathologies or diseases are difficult to monitor and be detected. For instance, it is important for clinicians to assess the cerebral well-being in patients suffering from a traumatic brain injury (TBI). Among other parameters, a crucial parameter is the intracranial pressure (ICP), which is the pressure inside the skull, since these patients have a risk of showing elevated ICP, which can lead to ischemia in the brain. However, this parameter is mainly measured invasively, by drilling holes in the skull of patients and inserting a probe deep in the brain. Therefore, this measurement is only done in patients with severe TBI.

Other solutions for monitoring ICP propose the use of non-invasive techniques. For instance, patent document U.S. Pat. No. 7,547,283-B2 discloses a technique consisting of acquiring and processing acoustic data. However, this kind of technique is only applicable to a select number of arteries and, in general, is sensitive to macro-vasculature, and cannot detect alterations affecting the microvasculature. Furthermore, the disclosed technique requires at least two variable inputs: arterial blood pressure and blood flow velocity measured with Transcranial Doppler (TCD), an ultrasound technique.

Other techniques make use of optical data to determine ICP non-invasively. In patent document WO2016164891-A1, diffuse correlation spectroscopy data is acquired using optical sensors, and pulsatile cerebral blood flow index is determined using the acquired data. However, this method requires acquiring additional physiological data (e.g. electrocardiogram data, electroencephalogram data, blood pressure data) from the subject using physiological sensors, and correlating the pulsatile cerebral blood flow with the physiological data from the subject.

As such, there is a need for a system and method that address these limitations, with further ability to detect any kind of disease causing altered pulsatile blood flow-like pressure on the vessels or blockage in the vessel (and therefore not limited to diseases of the brain such as the ICP)— that does not require acquiring and analyzing two or more input variables.

SUMMARY

The present disclosure refers to a new method and system for non-invasive monitoring and analysis of pulsatile blood flow changes in the local microvasculature as a biomarker for disease or other physiological phenomena. The method makes use of properties in the pulse contour, i.e. waveform, of pulsatile blood flow time series. The method can detect, categorize and score pathologies that influence pulsatile blood flow. Examples include increased pressure on the vessel (as in the case of intracranial hypertension), plaque buildup (which can hamper blood flow like in a stroke), or peripheral arterial diseases.

The system implements a new method for processing the blood flow signal and deriving indices from the information of the pulses without requiring the use of additional parameters, such as blood pressure. The system can include a high-data rate diffuse correlation spectroscopy device for acquiring high temporal resolution blood flow time-series data to resolve the pulsatile behavior of the blood flow with adequate signal-to-noise ratio. The diffuse correlation spectroscopy device makes use of electronics, light detectors and light sources that can be coupled to the tissue surface by contact or non-contact means, with or without fiber optics. The high-data rate diffuse correlation spectroscopy device employed is already state of the art (e.g. Parthasarathy et al., "Dynamic autoregulation of cerebral blood flow measured non-invasively with fast diffuse correlation spectroscopy", JCBFM, 2017).

In accordance with one aspect of the present invention, a computer-implemented method is provided for detecting and categorizing/scoring physiological phenomena or pathologies causing altered pulsatile blood flow. The method comprises the steps of receiving a pulsatile blood flow signal of a subject comprising at least one cardiac cycle, extracting a set of features from the pulsatile blood flow signal, and categorizing/scoring a pathology based on the extracted features.

The extracted features may be learned either through a machine learning algorithm or by deterministic means. The extracted features may be selected in the following list of features (but not limited to): systolic amplitude; diastolic amplitude; systolic to diastolic amplitude ratio; systole to diastole time difference of the same pulse; diastole of one pulse to the systole of the next pulse; systole full width half maximum (FWHM); diastole FWHM; slope of the diastole decline; slope of the systole decline; standard deviation of the systole; standard deviation of the diastole; or a combination thereof. The extracted features may be obtained via a time-frequency analysis.

The step of categorizing a pathology preferably comprises developing a discrete set of indices or a continuous index (score) measure for the pathology. In an embodiment, the step of categorizing a pathology is performed using a logistic based method based on determined set of features or a machine learning algorithm.

The step of categorizing/scoring a pathology based on the extracted features may comprise fitting a regression model or classifying the extracted features on a determined class from a discrete set of classes. The categorization of a pathology based on the extracted features may comprise using a set of thresholds on a feature (or combination of features) associated to different levels of severity of the pathology to obtain a discrete index representative of the severity of the pathology. The scoring of a pathology based on the extracted features may comprise a regression to a value of interest, with further normalization of extrema to bound the output between a range that determines severity of a pathology.

The method may comprise a preprocessing step applied to the pulsatile blood flow signal to obtain preprocessed data of the pulsatile blood flow signal, wherein the set of features are extracted from the preprocessed data.

According to an embodiment, the method may further comprise receiving a plurality of static features of the subject, wherein the pathology is categorized/scored based on both the extracted features and the static features.

The method may comprise the step of acquiring the pulsatile blood flow signal from a region of interest of the subject (using for instance a diffuse correlation spectroscopy device). The method may also comprise displaying the result of the categorization/score on a display.

In accordance with a further aspect of the present invention, there is a system provided for detecting and categorizing pathologies causing altered pulsatile blood flow. The system comprises a processing device including a processor and a computer-readable medium having encoded thereon computer-executable instructions to cause the processor to execute the computer-implemented method previously defined.

In an embodiment, the system further comprises a diffuse correlation spectroscopy device configured to acquire the pulsatile blood flow signal from a region of interest of the subject, said device comprising a plurality of optical sources, a plurality of optical detectors and a correlator. The system may further comprise a display, wherein the processing device is configured to display the result of the categorization on the display.

In accordance with yet a further aspect of the present invention there is a computer program product provided for detecting and categorizing pathologies causing altered pulsatile blood flow, comprising computer code instructions that, when executed by a processor, causes the processor to perform the method as previously described. The computer program product may comprise at least one computer-readable storage medium having recorded thereon the computer code instructions.

The present invention provides the following advantages:
- Requires only pulsatile blood flow as a real-time input to a classification/regression algorithm in order to provide an index/value as a biomarker. The present method only requires the pulsatile blood flow to be obtained by any available method that can resolve pulsatile blood flow, such as diffuse correlation spectroscopy (DCS) or Transcranial Doppler (TCD). Unlike the inventions disclosed in other prior art documents, it does not require additional physiological data provided by a physiological sensor. To that end, the present method analyzes and takes into account properties of the pulse contour of pulsatile blood flow data in a series of cardiac cycles, not only changes in the pulse amplitude. Categorization and scoring algorithms allow a classification, a continuous or discrete index metric of a pathology by relating pulse contours features to different levels of severity of a disease.
- The present method can be applied to any situation, physiological phenomena or disease where the pulsatile blood flow is altered by external factors, like pressure as in cases such as elevated ICP, narrowing or blockage of the vessels, as in cases such as plaque deposition, peripheral arterial disease (PAD) or stroke. The method non-invasively uses pulsatile blood flow as a biomarker.

One application of the invention is the non-invasive monitoring of pulsatile cerebral blood flow to analyze its pulse contour as an indicator for levels of intracranial pressure (ICP). The pulse shapes can be categorized as belonging to different levels of ICP by using different thresholds in the values of certain features in pulse shapes for defining severity levels (e.g. assigning thresholds that relate to either a normal, moderate, or severe level of ICP). The categorization of different levels of ICP can also be accomplished by using a feature extractor and classifier, such as a neural network, on the pulsatile blood flow signal to determine its class of severity.

Another situation where pulsatile blood flow can be altered is the case of peripheral arterial disease (PAD), where the blood flow is influenced and hampered by the narrowing of vessels due to plaque buildup in the arteries and arterioles. This also impairs the microvasculature. The new method can assess the physiological relation of the pathology by pulsatile blood flow using a single measurement on the leg.

Another application is the investigation of ischemic stroke patients, where the blood flow is altered due to a blocked vessel, which can also influence blood flow's pulse contour.

The project leading to this application has received funding from the European Union's Horizon 2020 research and innovation programme under the Marie Skłodowska-Curie grant agreement No 675332.

BRIEF DESCRIPTION OF THE DRAWINGS

A series of drawings which aid in better understanding the invention and which are expressly related with an embodiment of said invention, presented as a non-limiting example thereof, are very briefly described below.

FIG. 1 shows a typical pulse shape of pulsatile blood flow.

FIG. 2A shows an example of altered pulsatile blood flow.

FIG. 2B shows another example of altered pulsatile blood flow.

DETAILED DESCRIPTION

Figure 3:
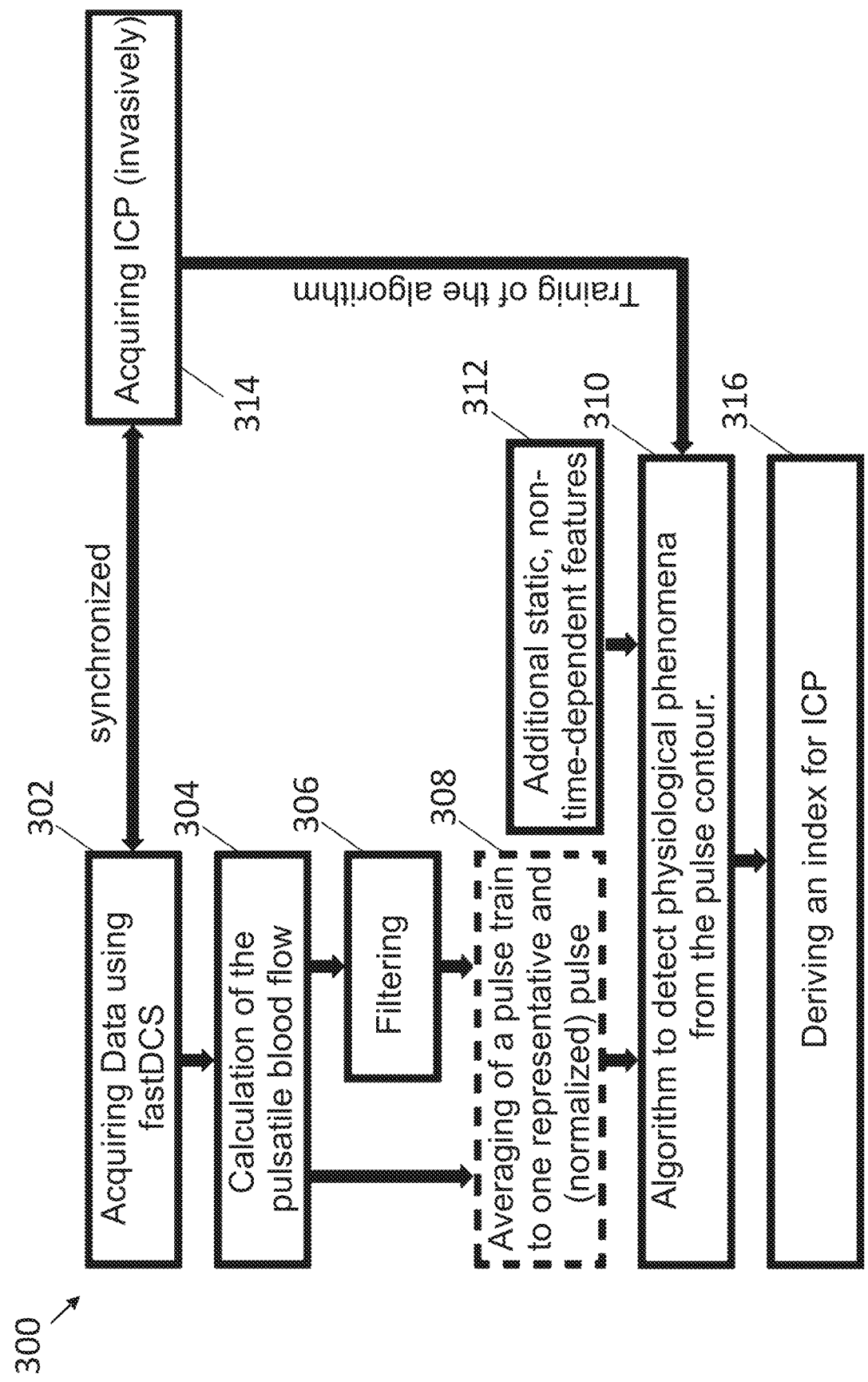
FIG. 3 represents a schematic flow chart of the data processing for the example of ICP.

The present invention refers to a system and a computer-implemented method for detecting and categorizing pathologies through an analysis of pulsatile blood flow.

FIG. 1 depicts the shape of a typical pulse 100 of the pulsatile blood flow containing information of the cardiac cycle including the systole and the diastole.

Diffuse optical techniques such as near-infrared spectroscopy (NIRS) and diffuse correlation spectroscopy (DCS) can provide non-invasive, continuous, bed-side measurements of different physiological parameters. DCS is an optical technique to measure deep (up to centimeters) microvascular blood flow. DCS employs near-infrared light to probe tissue; due to the multiple scattering effects in the tissue the remitted light can be detected. In order to probe the tissue, light can be injected into the tissue via fiber optics. Within a certain distance, photons that travel through the tissue are detected with fiber optics and are subsequently sent to a detector. A class of detectors detect single photons and emit signals to a hardware correlator or a software correlator implemented by a processing unit. One implementation of DCS uses a correlator, which calculates the normalized intensity autocorrelation function, which contains information about blood flow. Blood flow can be inferred by means of applying a model for the motion of the scatterers (e.g. red blood cells) that the injected light interacts with or by means of a single data point in the correlation curve. The technique can also be applied as a non-contact technique without fiber optics. The acquired autocorrelation follows approximately an exponential decay, where the decay rate relates to the flow. If the acquired autocorrelation curve decays quickly, high blood flow is detected. If the decay rate is low, the blood flow is also low. If the correlator is able to sample autocorrelation curves with a sufficiently high sampling rate, the blood flow signal can resolve topological structures that relate to that cardiac cycle (as shown for instance in FIG. 1, representing the shape of a typical pulse 100 of the pulsatile blood flow). In a case where pulsatile blood flow needs to be resolved, a high-data rate DCS (or fastDCS) is employed. The pulse 100 contains information about the systole 110 and the diastole 120. In the systole 110, the peak is called systolic peak 112 and the peak during the diastole is referred to as diastolic peak or second peak 122. The dicrotic notch 130 separates systole 110 and diastole 120. FIG. 1 also represents the end diastolic flow 124 that separates the adjacent pulses 100. The second peak 122 is due to reflections on the vessel wall and depends on the compliance of the vessels. The pulsatile blood flow can be influenced by external factors such as pressure from the outside on the vessel or changes within the vessel, like plaque, which leads to narrowing of the vessel.

Apart from the described DCS method, other optical techniques can be used to measure sub-surface blood flow based on the laser speckle statistics. These techniques rely on the movement of the scatterers (mainly red blood cells in human tissue) affecting the statistics of the observed speckle pattern. Different illumination methodology, detection technology and/or analysis methods may differentiate these techniques. For example, the aforementioned intensity or the electric field autocorrelation function can be calculated for at least one delay time to quantify differential blood flow, as in the case of the modified beer lambert law. Other approaches may measure speckle contrast, defined as the standard deviation of intensity (over space and/or time) divided by the mean intensity (over space and/or time), as in the case of speckle contrast optical spectroscopy/tomography (SCOS/SCOT). Yet another approach may be based on calculating the spectral broadening or shift as a Doppler effect. Examples of other techniques include laser speckle flowmetry (LSF) (also known as laser speckle contrast imaging (LSCI), diffuse speckle contrast analysis (DSCA), speckle contrast DCS (scDCS), laser Doppler flowmetry and interference diffuse wave (or correlation) spectroscopy (iDWS/iDCS). Other techniques may resolve the optical path length of detected photons and turn that into information about blood flow and tissue optical properties, as in the case of time domain diffuse correlation spectroscopy (TD-DCS) and interferometric near-infrared spectroscopy (iNIRS). All these methods enable the acquisition of similar signals as described in this invention.

FIGS. 2A and 2B shows two examples for external factors influencing the pulse shape of the pulsatile blood flow. In both cases, the inflow is a typical pulse 100 and the outflow is an altered pulse 200 where the shape of the typical pulse 100 is substantially changed (e.g. a reduced amplitude of the second peak 122). The example of FIG. 2A corresponds to external pressure 210 applied over the vessel 202, altering the pulsatile blood flow. In FIG. 2B narrowing of the vessel 220 (produced for instance by a plaque buildup 204) can lead to an altered pulse shape. The herein described causes for alterations in the pulse contour are non-limiting examples.

In the case of external pressure 210, a common example is intracranial pressure (ICP) in the brain. Within the vessel 202, arterial pressure (AP) pushes blood against the vessel walls from the inside, while ICP pushes from the outside. Even though ICP is much smaller than AP, both pressures are influencing blood flow. If ICP is high, this will lead to a decrease in both diastolic pressure and blood flow. Generally, a change in the pulse shape of the flow can be observed.

The method of the present invention analyzes the pulse contour of the acquired pulsatile blood flow to determine the cause (pathology, disease or situation) of the altered pulse 200. Different methods may be used for this analysis, such as calculating ratios of height to width of different components of the pulse (the pulse being either a measured pulse or an averaged pulse obtained from a measured train of pulses) or learning and extracting relevant features in the pulse contour using a machine learning algorithm. Other methods may include fitting the pulse contour of the blood flow to a biological model, or the analysis of the pulse shape and the different components of the pulse in the time or frequency domain. Further algorithms may be used, such as machine learning algorithms, to assess the pulse contour of pulsatile blood flow and categorize it into different classes or to build an index/score of affected physiology. In other words, this will allow us to categorize the severity of a disease, to decompose the physiological phenomena into sub-classes or to detect a disease.

Changes in the pulse contour in pulsatile blood flow can be caused by a situation, disease or physiological phenomena. This permits further analysis of the pulsatile blood flow to report an index, a score or a categorization of a biomarker of interest. For example, if ICP is increased (hypertension), the shape of the altered pulse 200 can display dampening in the diastolic or second peak 122 due to high extravascular pressure on vessel 202. Using comparative analysis with invasive measurements, calibration of the method can be done to classify or build an index relating different pulse contours with different levels of ICP (e.g. normal, moderate or severe).

FIG. 3 depicts a flowchart diagram for processing data as performed by the proposed method 300 for detecting and categorizing pathologies, according to an embodiment applied to ICP. In this example, applied to an application to detect and categorize ICP, optical data is acquired 302 and pulsatile blood flow is calculated 304. Depending on the quality of the pulsatile blood flow signal, filtering 306 of the signal may be applied. For instance, linear filters can be used to obtain a denoised pulse shape. Optionally, a series of pulses in a pulse train from the pulsatile blood flow signal within a specific time period can be averaged 308 to one normalized pulse. This signal is fed to a classifier to classify 310 the pulse contour. An example of a classifier may be a machine-learning algorithm such as an artificial neural network, although the algorithm does not need to be based in machine learning (for instance, thresholds for certain extracted features may be used instead). The pulse contours can then be classified, or an index can be developed, according to the pulse contour's features.

Additionally, the algorithm for categorizing or scoring pathologies may consider time independent features 312 like age, risk factors, anatomical data or even physiological data. Time independent features 312 are concretely variables that do not vary in short term (i.e in the time frame of the data acquisition). In the case of time independent physiological data, like blood pressure data, the meaning of "time independence" comes from the fact that a static measurement was made at the beginning of the data acquisition and was not a variable of time, such as the pulse contour in pulsatile blood flow.

The algorithm may be trained with invasive measurements of ICP 314 as labels synchronously acquired alongside with the fast DCS blood flow data acquisition 302. The algorithm 310 can analyze the pulse contour by a method that looks at either predetermined features like different ratios of peaks in the pulsatile blood flow data pulse dynamics in time amplitudes, or a method that uses learned features from a machine learning algorithm. Based on a combination of features given to the algorithm, a severity index can be derived 316 and given as an output. The index can contain information about the level of ICP of the subject, such as elevated ICP, moderately elevated ICP or normal ICP. No absolute values are provided.

Figure 4:
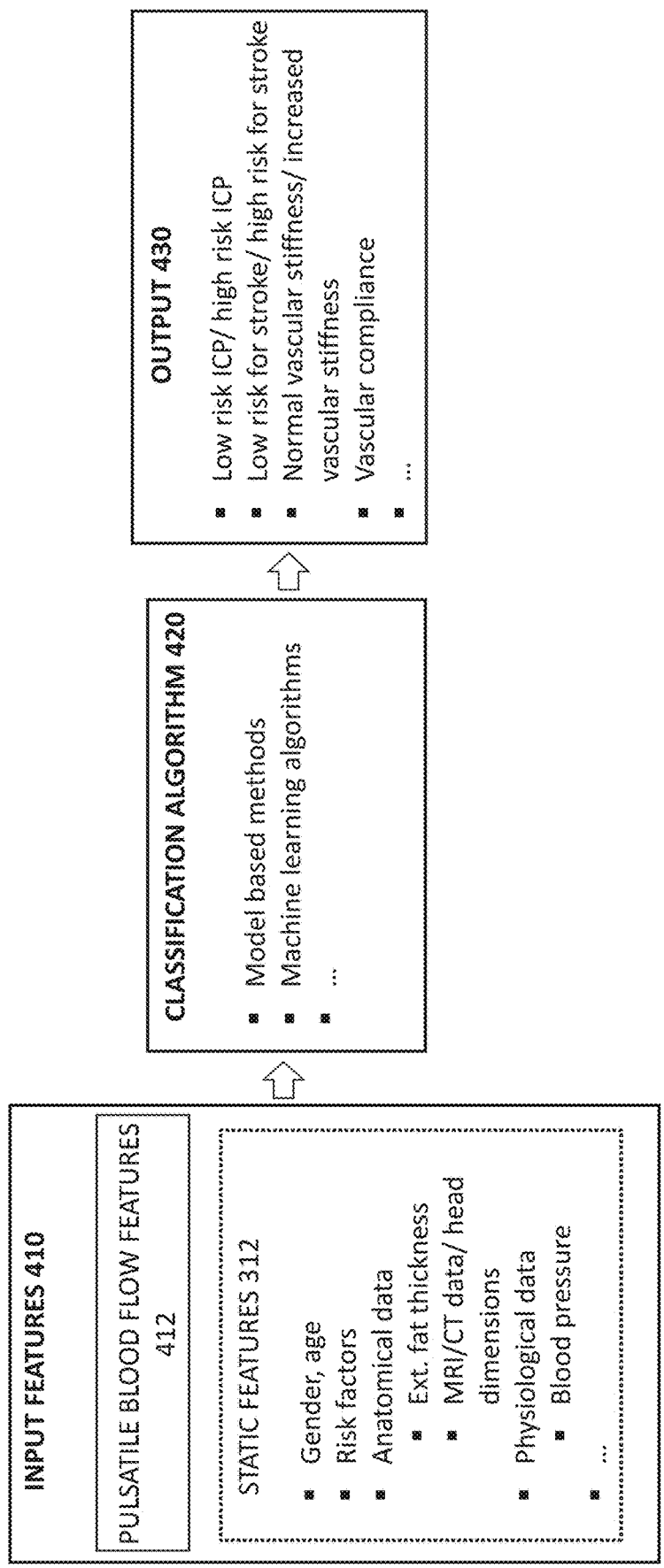
FIG. 4 is a schematic view of the possible input features, smart classification algorithms and output indices used.

FIG. 4 gives a general overview of different input features 410 which can be used by the algorithm 420, and possible outputs 430 of said algorithm. The algorithm 420 may include, among others, model based methods or machine learning algorithms. For instance, any one of the following machine learning algorithms may be employed:

Artificial neural network

Convolutional Neural Networks, or Time Delay Neural Networks (Learning shift invariant patterns in time).

Recurrent Neural Networks, like Long-Short Term Memory (Learning based on nonlinear combinations of contextual information for time points).

Deep belief network (generative model that maximizes joint probabilities from sampling an input to achieve an output).

Spiking neural networks (activation of neurons model use ordinary differential equation models for membrane capacitance of neurons).

Clustering algorithm (no labels/finds a pattern in dataset).

Support vector machine (Projection of features in higher dimensional vector space to linearly separate classes).

Reinforcement learning (learning optimal parameters by iterating through a set of policies that determine an output, choosing the optimal policy that maximizes rewards defined by an algorithm)

Genetic algorithm (Sample parameters from a probability density function (PDF), mutating a PDF over iterations of training "episodes" to converge to optimal PDF from which to sample parameters)

Autoregressive moving average (statistical inference).

The input features 410 at minimum include features 412 extracted from pulsatile blood flow signal. Input features 410 may also include one or more static features 312, as previously explained (e.g. gender, age, risk factors, anatomical data, physiological data). The output 430 can either be a score or category, depending on the algorithm or the specific physiological phenomena of interest, and may include indices related to ICP (e.g. low risk ICP, high risk ICP), stroke risk (e.g. low risk/high risk), stiffness of the vessels or vascular compliance (e.g. normal/increased), among other possible pathologies.

The algorithm, which in the example of FIG. 3 is based on ICP measurements, can also be applied to other pathologies, which alter the contour of pulsatile blood flow. For instance, in peripheral arterial disease (PAD) the arteries are narrowed and stiffened by plaque. This also influences blood flow in different compartments such as the arterioles. The pulse contour is also changed due to the stiffened vessels. Given all that, the blood flow can be hampered. Analysis of the pulse contour with the described method allows a report of an index of severity for this disease as well.

Other scenarios arise in ischemic stroke patients. In those patients, a vessel is blocked and blood flow is hampered. This also has an influence on the surrounding microvasculature, changing the dynamics of blood flow. Applying the analysis proposed in the described method allows an assessment of the severity of stroke in the patient that would help to characterize the local effects of the stroke in different regions such as those due to the formation of an edema in the patient using optics.

Generally, measurements of pulsatile blood flow as a biomarker with an analysis of the pulse contour by the proposed algorithm can be used as an indicator for the severity of diseases which show altered pulsatile blood flow due to extravascular influences. Additionally, different thresholds in the index provide clinicians with a traffic light signal in their assessment of blood flow. Further analysis during mild challenges like cuff inflations as a stimulus allow an investigation into the evolution (e.g. delay time, time to recovery) of physiological reactions to such stimuli, for example, using the recovery time of the pulse-shape to that during the baseline. This allows for direct insights into the dynamic compliance and regulation of the vasculature and can further provide additional information that can be used for pre-training a model in a patient with an evolving condition.

Figure 5:
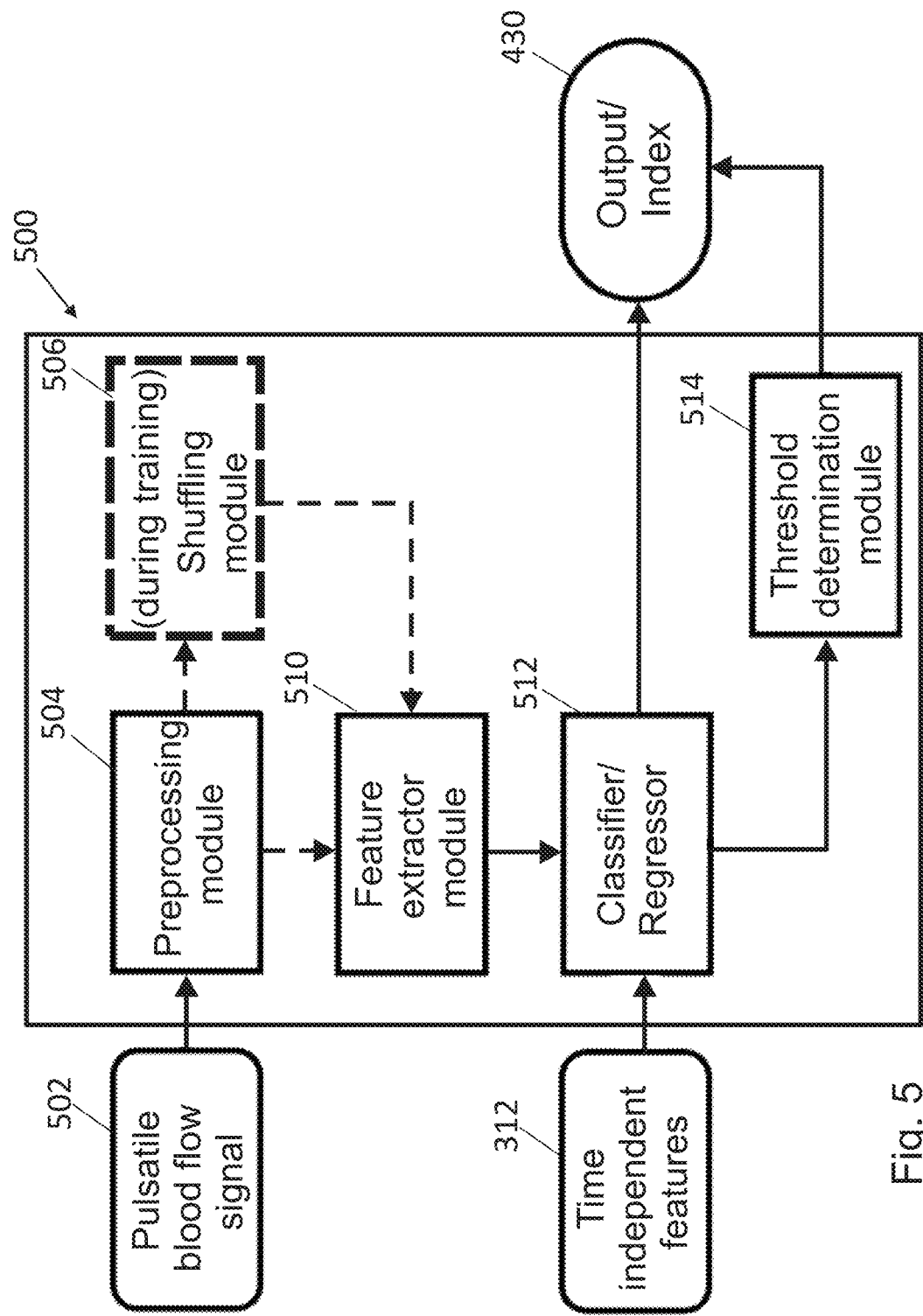
FIG. 5 is a diagram of a system implementing the method.

FIG. 5 depicts, according to an embodiment, a diagram of a system 500 for detecting and categorizing pathologies that cause an altered pulsatile blood flow. According to the diagram, a pulsatile blood flow signal 502 of a subject is received and preprocessed by a preprocessing module 504.

The pulsatile blood flow signal 502 is a windowed time series of pulsatile blood flow data points comprising at least one cardiac cycle. The pulsatile blood flow signal 502 is used as input to the preprocessing module 504. From the windowed time series, a set of preprocessing steps can optionally be carried out by the preprocessing module 504 to obtain a signal with better bias and minimal variance. The preprocessing steps may include:

Linear detrend to remove any drift in the signal.
  Filters on the blood flow to focus on particular frequency spectral ranges.
  Normalization of the time windows of any kind depending on the application, such as Z standardization, or min-max normalization.
  Averaging of pulses to further increase the SNR and reduce the dimensionality of the pulse contour.
  Whitening, such as zero-phase whitening, of feature sets to decorrelate features in the population to better tune into samples of significance for the classifier.

When training the algorithm, a population of preprocessed window samples are randomly shuffled by a shuffling module 506 to aid in the stochastic gradient optimization algorithm for finding the optimal network weights. Otherwise, each window can be passed into the algorithm independently, as one would do in a real-time application.

The preprocessed data is then sent into a feature extractor 510. A set of features are extracted by the feature extractor module 510 from the pulsatile blood flow signal (in this case, by analyzing the preprocessed data).

The extraction of the features applied by the extractor module 510 can be of a deterministic kind or, alternatively, the features can be learned through a machine learning model. Of the deterministic kinds, the selected features may be, but not limited to, any of the following (or a combination thereof):

Systolic amplitude.
  Diastolic amplitude.
  Systolic to diastolic amplitude ratio.
  Systole to diastole time difference of the same pulse.
  Diastole of one pulse to the systole of the next pulse.
  Systole full width half maximum (FWHM).
  Diastole FWHM.
  Slope of the diastole decline.
  Slope of the systole decline.
  Standard deviation of the systole.
  Standard deviation of the diastole.

The feature extractor module 510 may also extract features via a time-frequency analysis. Some examples include, but are not limited to:

Peak frequency of a set amount of overlapping frequency bands.
  The spectral centroid of a set amount of frequency bands.

The feature extractor module 510 may also learn features through a machine learning algorithm. Of the learning models, the following algorithms, among others, may be used to decompose the time series to a number of features:

Hidden Markov models.
  K-nearest neighbors of time windows.
  Distance of time window vectors to centroids from a K-means algorithm.
  A set number of 1D temporal kernel filters in a convolutional filter.
  Stacked auto encoder for learning lower dimensional and higher order encodings of a time series vector.
  Restricted Boltzmann machines to develop a generative model that maximizes the probability of constructing data from the input layer by sampling a lower dimensional hidden layer.
  Long-Short Term Memory Cells or Gated Recurrent Units to learn a hidden state vector that is parsed from a time series alongside contextual information at each time step.

The optimal features to be extracted can be defined by methods of cross validation.

Once the features are determined, the extracted features are passed to a classifier 512 (or a regressor) to glean either a discrete set of classes that correspond to an input data set or a score derived by from a regression model. In some embodiments, the feature extractor module 510 may be part of the classifier 512, so that the features are actually extracted intrinsically from the classifier or regressor 512 itself (for instance, the preprocessed pulsatile blood flow data may be directly inputted into the classifier/regress, e.g. a Convolutional LSTM neural network).

The input data set of the algorithm 512 is the input features 410 including in this example the pulsatile blood flow data conveniently processed (i.e. the features extracted by the feature extractor module 510, the pulsatile blood flow features 412) and the static or time independent features 312 (the latter features 312 being optional). Therefore, apart from the extracted features from the pulsatile blood flow, there may also be time-independent characteristics of an individual such as gender, age, risk factor (smoking, etc.), blood pressure, etc. that may provide a bias shift to the resulting output of the classification or regression model.

The classifier 512 may use any known classification algorithm, such as (but not limited to):

Neural network to output a set of sigmoidal outputs corresponding to the log likelihood of a class given an input data set.
  Decision tree or an ensemble Random Forest algorithm to parse which features provide highest entropy towards the decision of a certain output.
  Support vector machine to use a kernel transform to pass the feature set to a higher dimensional space where one can find a vector that linearly separates classes and maximizes the distance between that vector and the two classes.

For a regression task, the regressor may use any known regressor algorithm such as (but not limited to):

Neural network to output a prediction of the expected value, learned by minimizing a quadratic objective function like a mean squared error.
  An autoregressive moving average which models error as a wiener process, finding parameters of weights for current and prior time inputs that can minimize the variance of that wiener process, further filtered by a moving average.

The classifier 512 categorizes a pathology based on the extracted features, calculating an output 430 which may be an index that represents the classification of the shape of the pulsatile blood flow signal. If using a regressor, the output is the value of a function (for example, the regressor may be a learned system that transforms blood flow into a value representing physiology or an index of physiology). In the example of a neural network with a set of sigmoidal outputs, to obtain a certain discrete set of classes that describe an output, one may select an output from aforementioned set to determine the class that an input window belongs to. Predictions are made on each independent window.

The system 500 may optionally include a threshold determination module 514. A threshold can be determined by the threshold determination module 514, for example by an Receiver Operator Curve (ROC), to optimize certain specificity of sensitivity parameters. For example, given a likelihood output of the sigmoidal neuron output for a class that presents highest likelihood, determine the value of that likelihood that minimizes sensitivity while still providing high accuracy. If it is less than the desired likelihood to make a conclusive decision, the result is rejected; otherwise, the result is accepted.

A model will need to be retrained for determining a new objective, such as determining a different pathology. Not only will the model need to be retrained, but also certain hyper-parameters (such as batch size, weight decay regularizer, learning rate, number of extracted features, or even selected time-independent parameters) may need to be tuned for determining that new pathology.

Figure 6:
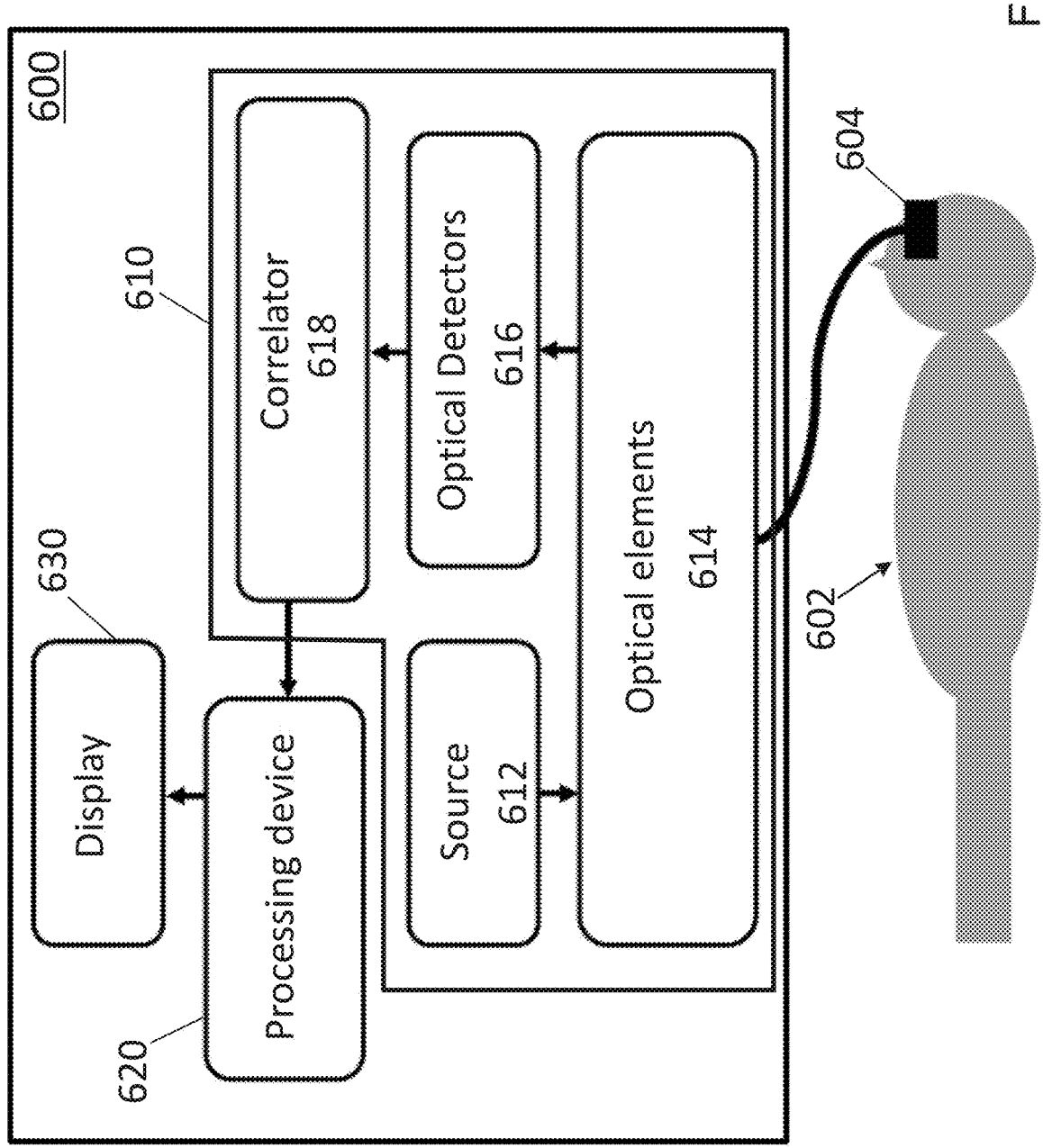
FIG. 6 depicts a schematic design of the system, according to an embodiment.

The described method for detecting and categorizing pathologies can either be implemented as a hardware algorithm (e.g. on an FPGA or other embedded processors) or as a software algorithm (e.g. on a computer or a cloud. FIG. 6 shows, according to an exemplary embodiment, a schematic design of a system 600 for detecting and categorizing pathologies.

The system 600 comprises a non-invasive, high-data rate diffuse correlation spectroscopy device 610 configured to acquire a pulsatile blood flow signal 502 from a region of interest 604 (e.g. the head) of a subject 602. The diffuse correlation spectroscopy device 610 comprises a plurality of optical sources (implemented by a source 612 and a plurality of optical elements 614, such as optical fibers), a plurality of optical detectors 616 and a correlator 618.

The source 612 is usually a laser in the near-infrared regime of wavelengths, although other sources may be used. The optical coupling to the region of interest 604 can be done with optical elements 614 like fibers, which are gathered together in a certain geometry on a probe applied to the patient or subject 602. Furthermore, the measurement can be done in a non-contact manner, where a laser might be shined directly to the region of interest 604 and the light detected directly by a plurality of optical detectors 616 with certain optical elements. The number of optical detectors 616 is flexible.

The correlator 618 can be either a hardware correlator (e.g. based on an FPGA which calculates the autocorrelation function directly), or as a software correlator, where the arrival of the photons can be time tagged, from which and autocorrelation function can be calculated via software (e.g. on a computer) based off this time-tagged data. Therefore, the correlator 618 depicted in the embodiment of FIG. 6 as a hardware correlator, may instead be included in the processing device 620 (software correlator). Since the method can be applied directly as a hardware algorithm, in the case of a hardware correlator using a FPGA, the fitting and classification can be done on the FPGA as well. The correlator may also be limited to the calculation of the changes of the correlation function at a single point.

In the embodiment shown in FIG. 6, the detection and categorization of pathologies is implemented on a processing device 620, such as a computer, a laptop, FPGA, or even a cloud computing system. The system may also comprise of a screen or display 630 where information like the calculated index and other results can be displayed. The display 630 can be the own screen of the processing device 620.

Figure 7A:
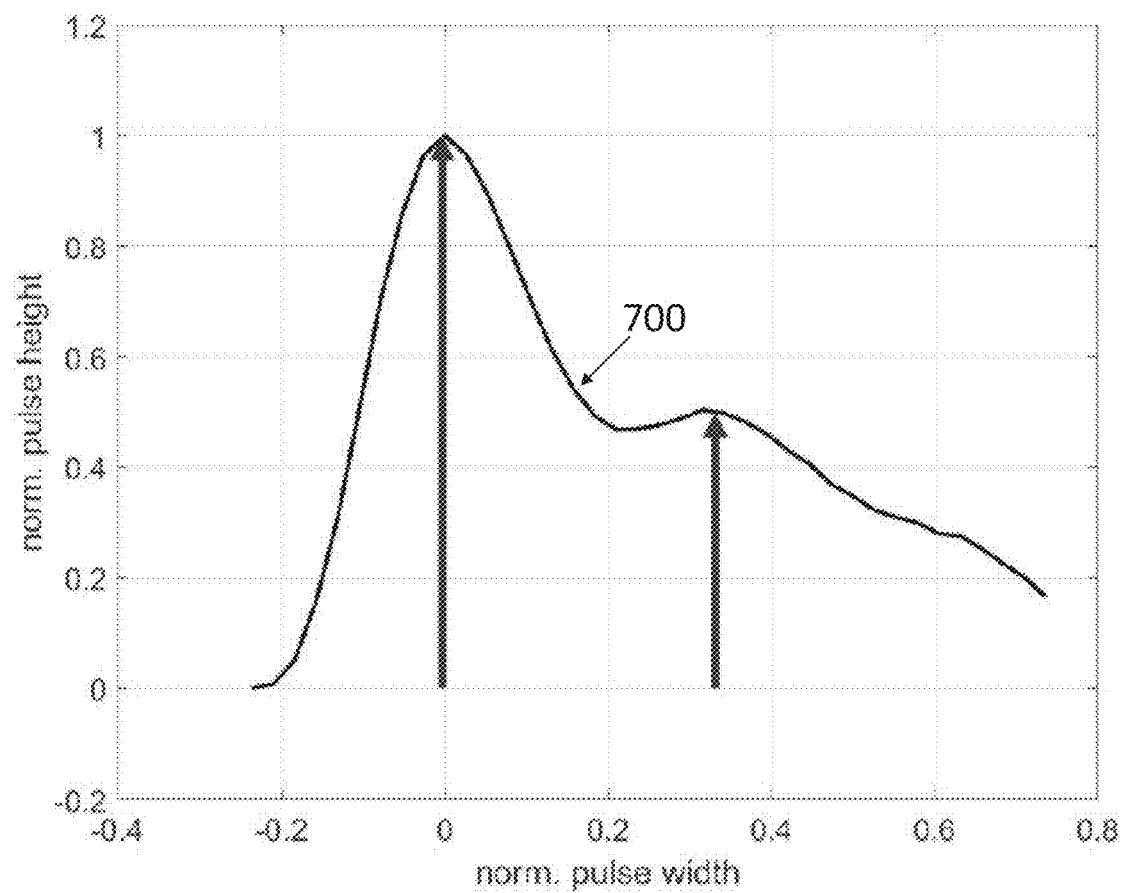
FIG. 7A shows an example of a feature extracted from a pulse of the pulsatile blood flow, such as pulse height of systole and diastole and/or ratio of both.

FIGS. 7A to 7H show schematic examples of an analysis on the pulse contour using a set of features extracted by a deterministic feature extractor module 510. Although not strictly necessary, the pulse 700 is generally normalized for this analysis. All these examples in FIGS. 7A to 7H are shown on a normalized pulse shape, but the x-axis can also be a time. These examples can be applied as features in the machine-learning algorithm or in a simpler way considering a threshold which can be applied. The index can be developed based on how pronounced a feature is in the signal. A combination of the different features could also be considered relevant for developing this index. Furthermore, a measure of deviations in these features from a set of pulses (as measured by standard deviation) could itself also be included in a feature set. Additionally, different ratios can be considered as well. The examples of features extracted are:

Pulse height of systole and diastole and/or ratio of both (FIG. 7A).

Figure 7B:
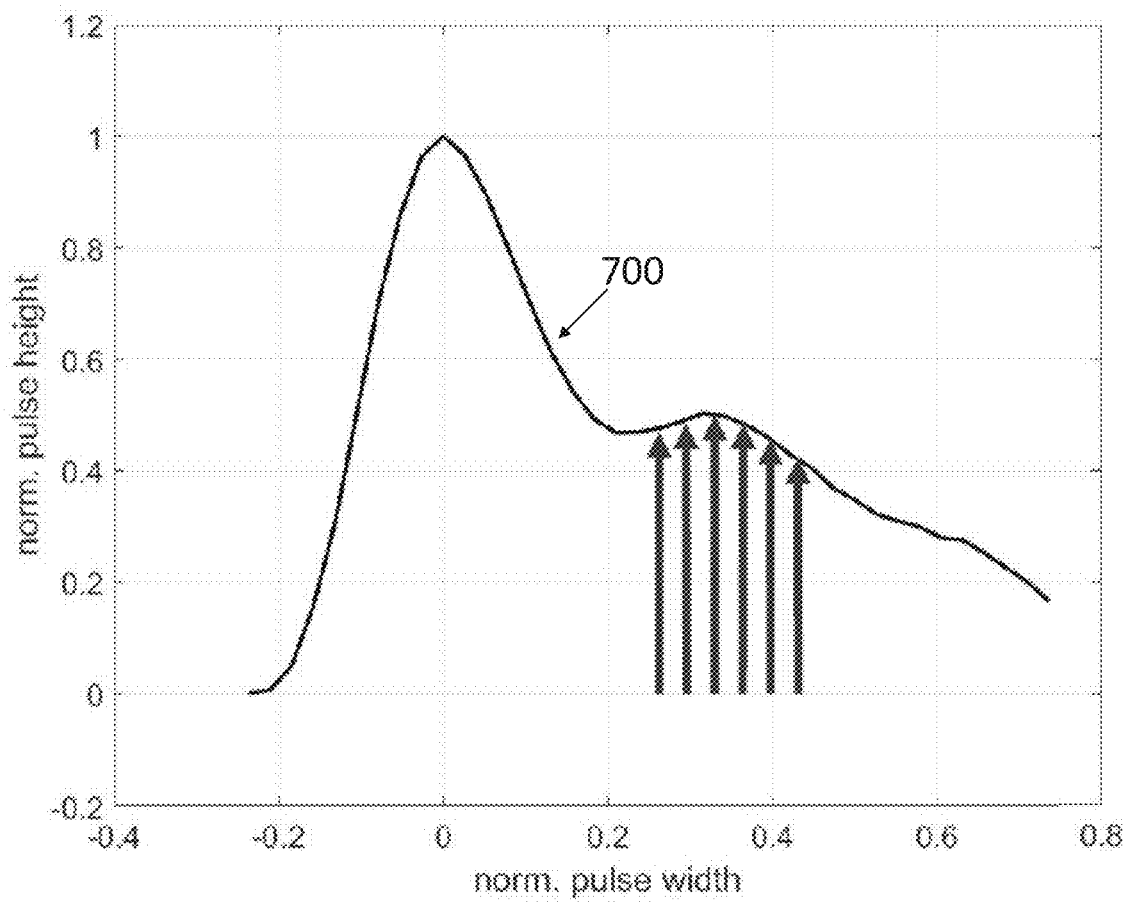
FIG. 7B shows pulse height of the diastole for different time feature extracted from a pulse of the pulsatile blood flow.

Pulse height of the diastole for different times (FIG. 7B).

Figure 7C:
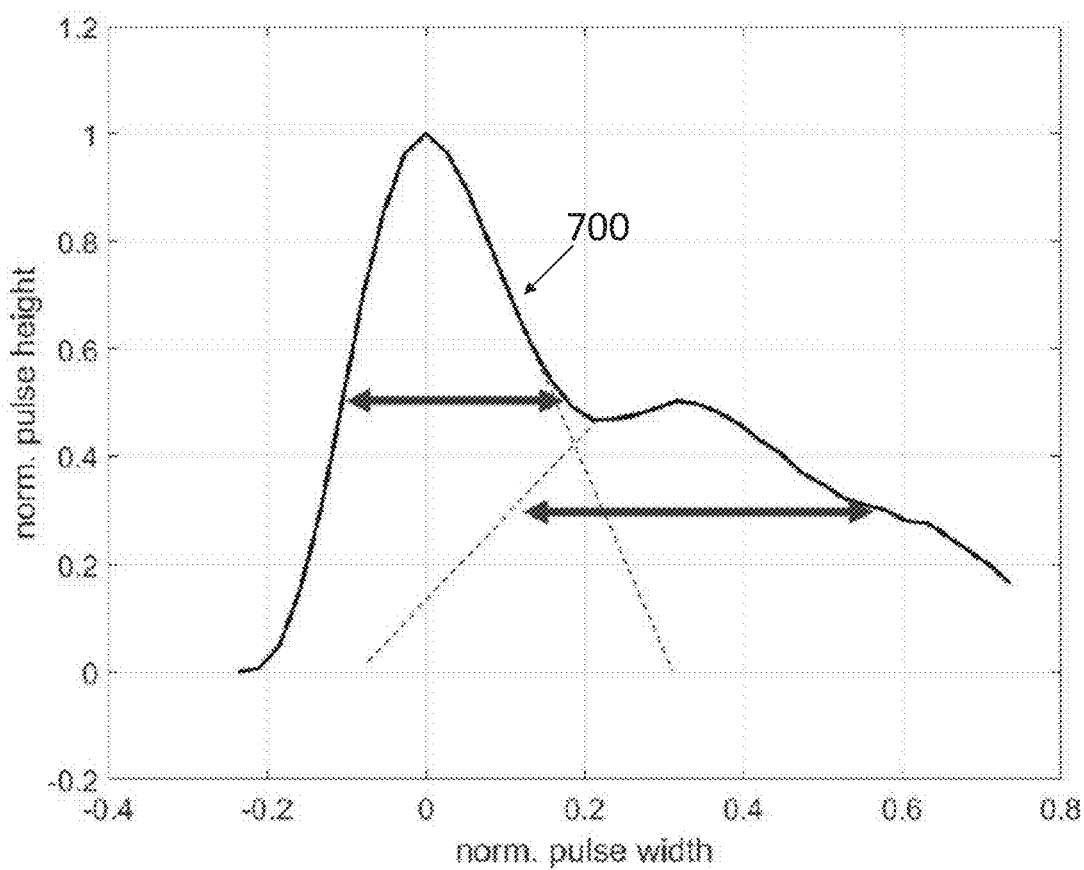
FIG. 7C shows full width half maximum of systole and/or diastole feature extracted from a pulse of the pulsatile blood flow.

Full Width Half Maximum of systole and/or diastole (FIG. 7C).

Figure 7D:
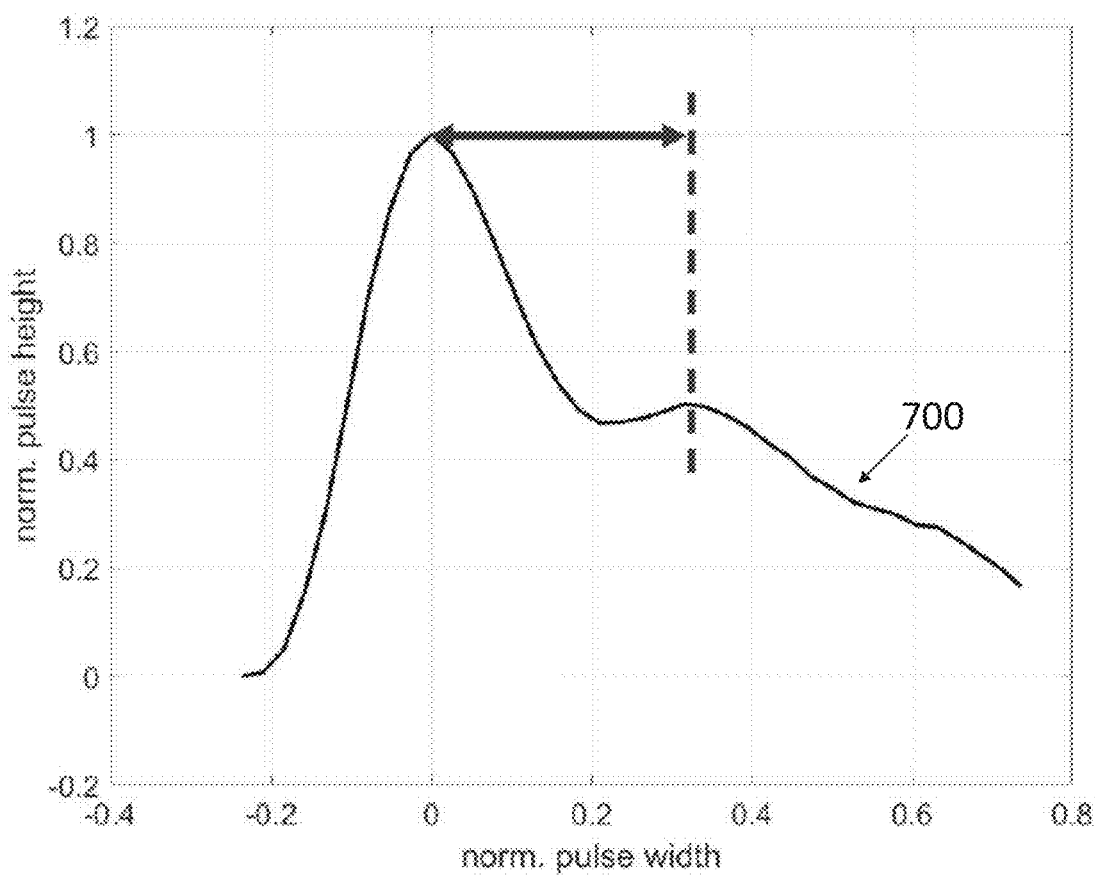
FIG. 7D shows time between systolic and diastolic peak feature extracted from a pulse of the pulsatile blood flow.

Time between systolic and diastolic peak (FIG. 7D).

Figure 7E:
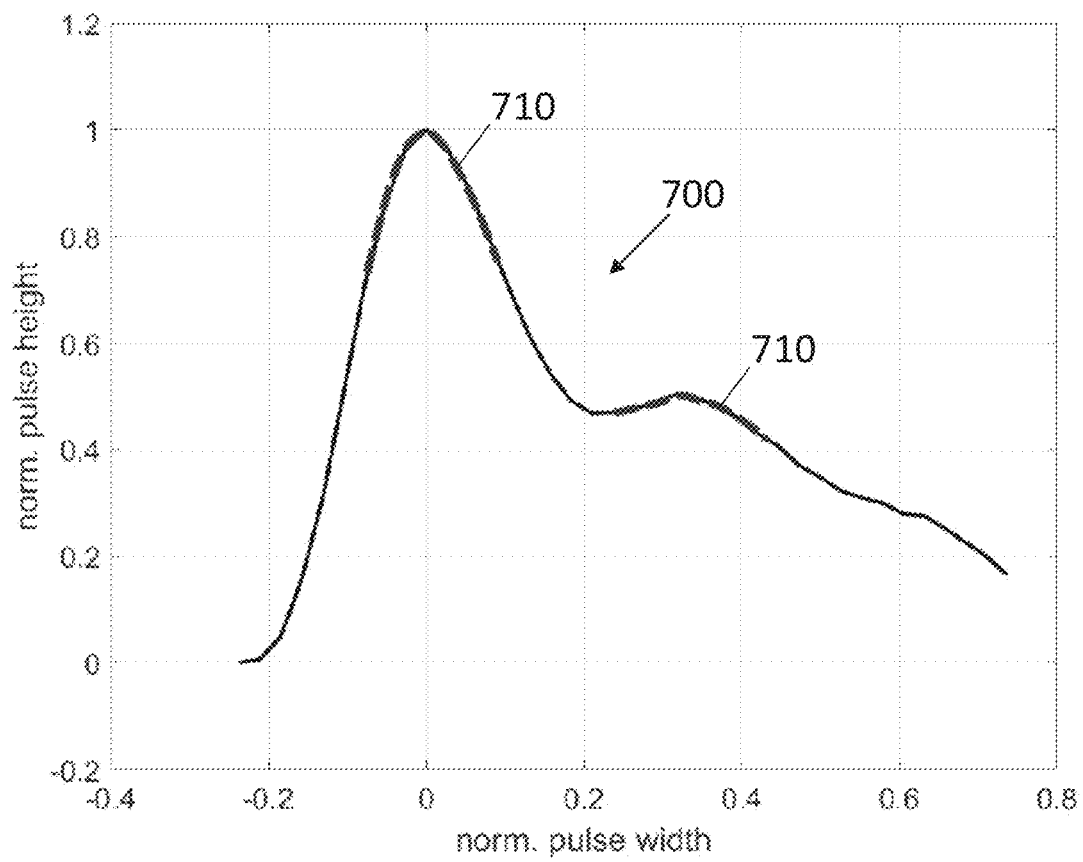
FIG. 7E shows fit of the peak of systole and diastole feature extracted from a pulse of the pulsatile blood flow.

Fit of the peak of systole and diastole (e.g. parabolic, fit to a parabola 710 shown in dotted lines) (FIG. 7E).

Figure 7F:
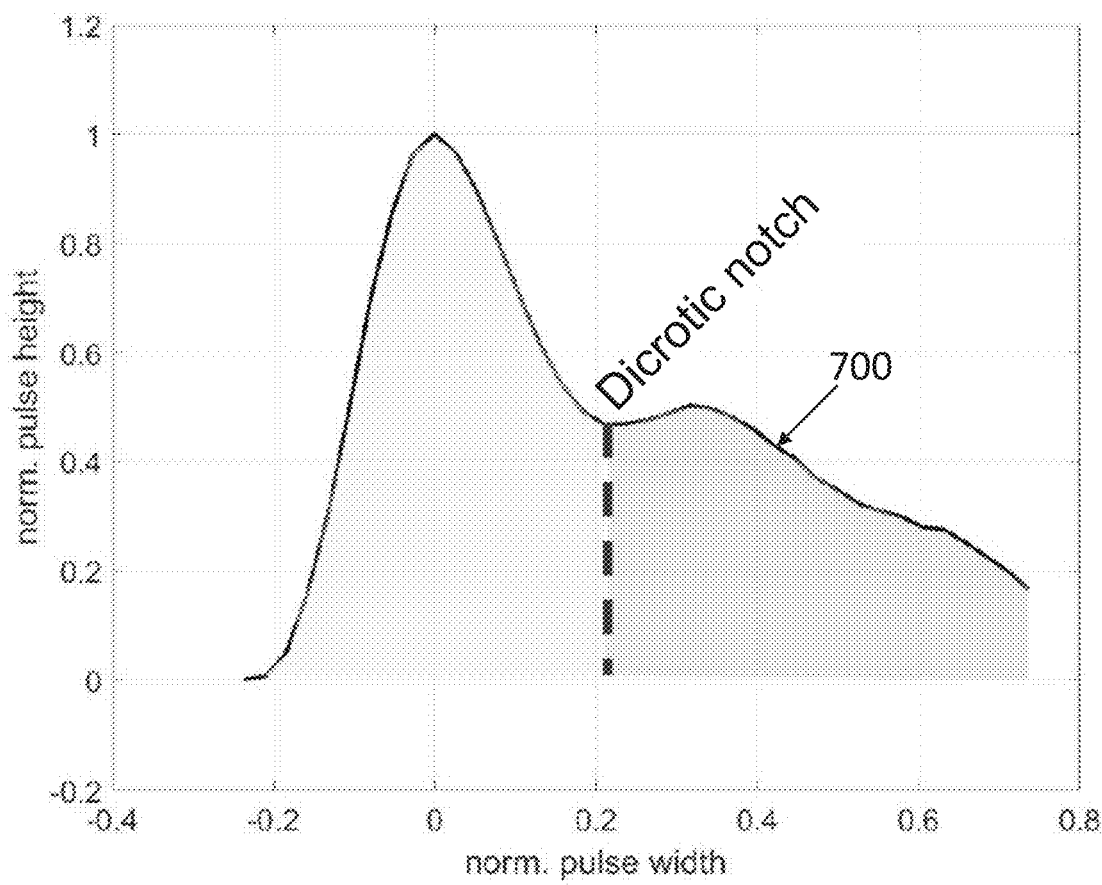
FIG. 7F shows area under the curve of systole and diastole and/or ratio of both feature extracted from a pulse of the pulsatile blood flow.

Area under the curve of systole and diastole and/or ratio of both (FIG. 7F).

Figure 7G:
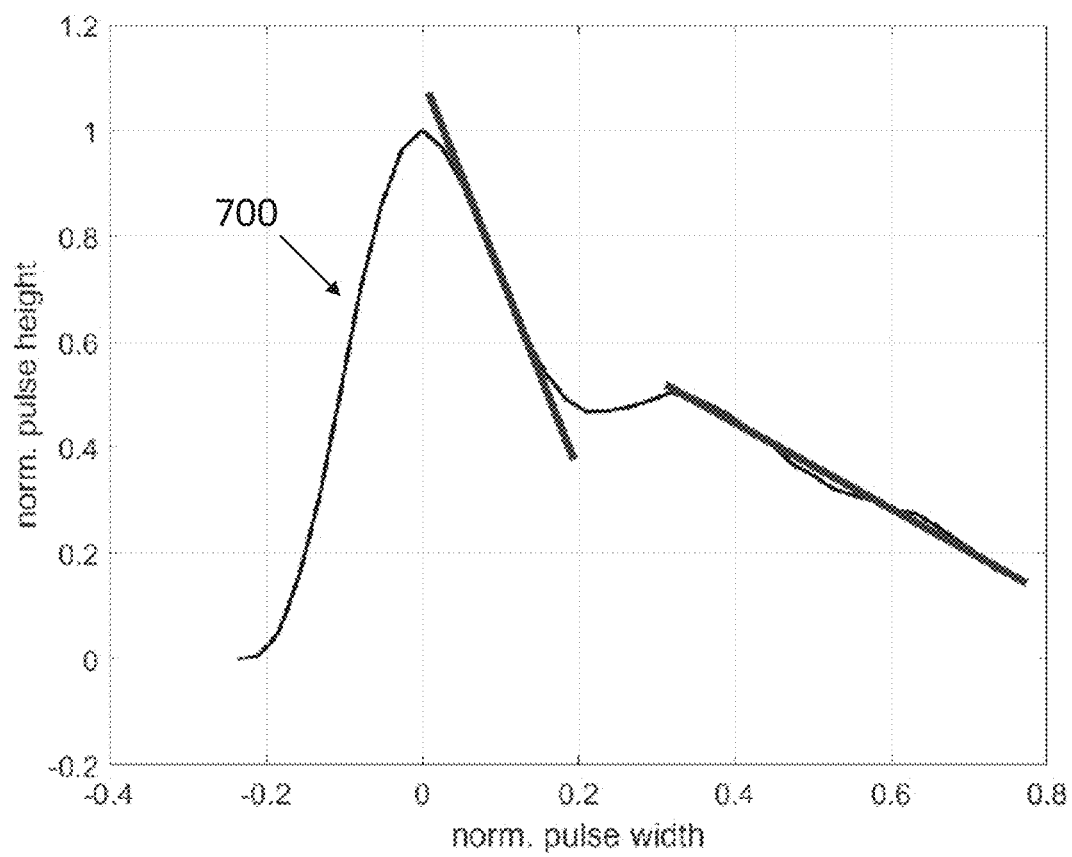
FIG. 7G shows slope of the rising and/or falling edges of the systolic and diastolic peak feature extracted from a pulse of the pulsatile blood flow.

Slope of the rising and/or falling edges of the systolic and diastolic peak (FIG. 7G).

Figure 7H:
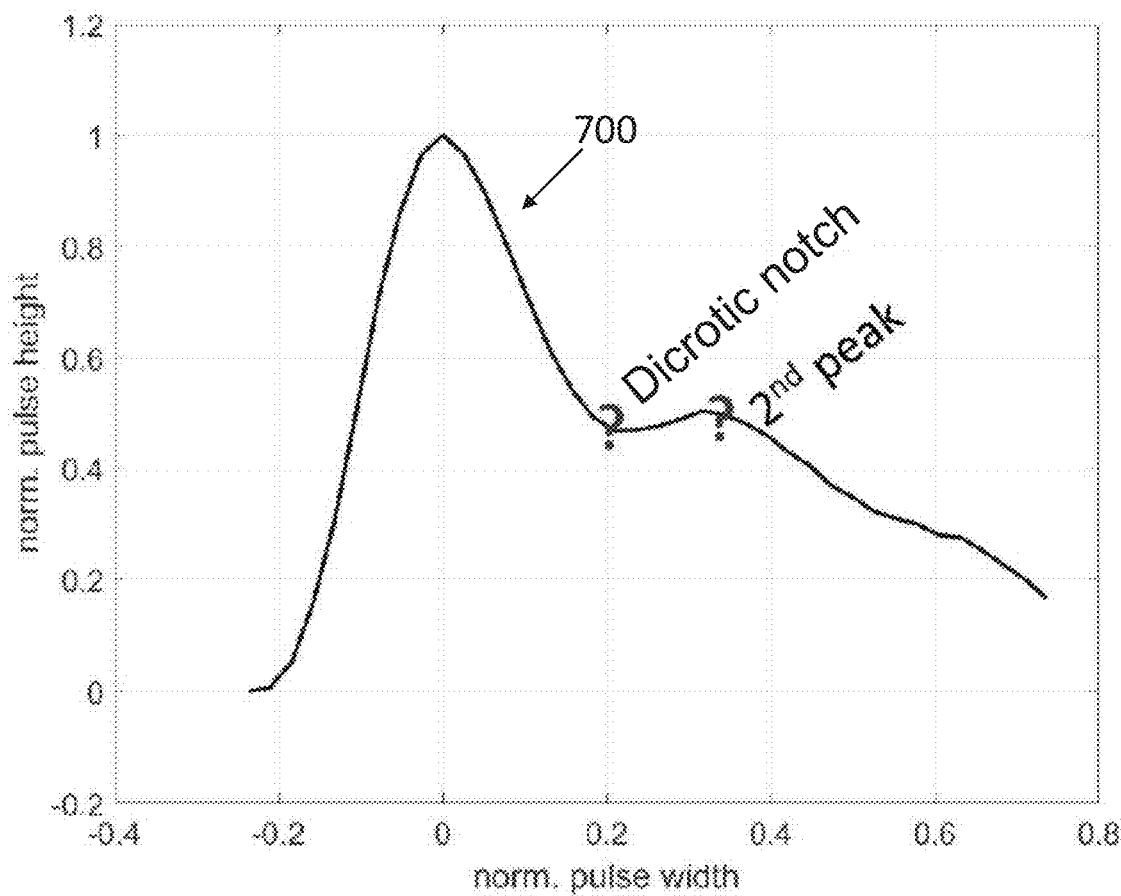
FIG. 7H shows dicrotic notch and diastolic peak feature extracted from a pulse of the pulsatile blood flow.

Dicrotic notch 130 visible or not visible. Second peak 122 visible or not visible (FIG. 7H).

Derivation of the pulse shape (not shown in figures).

Figure 8:
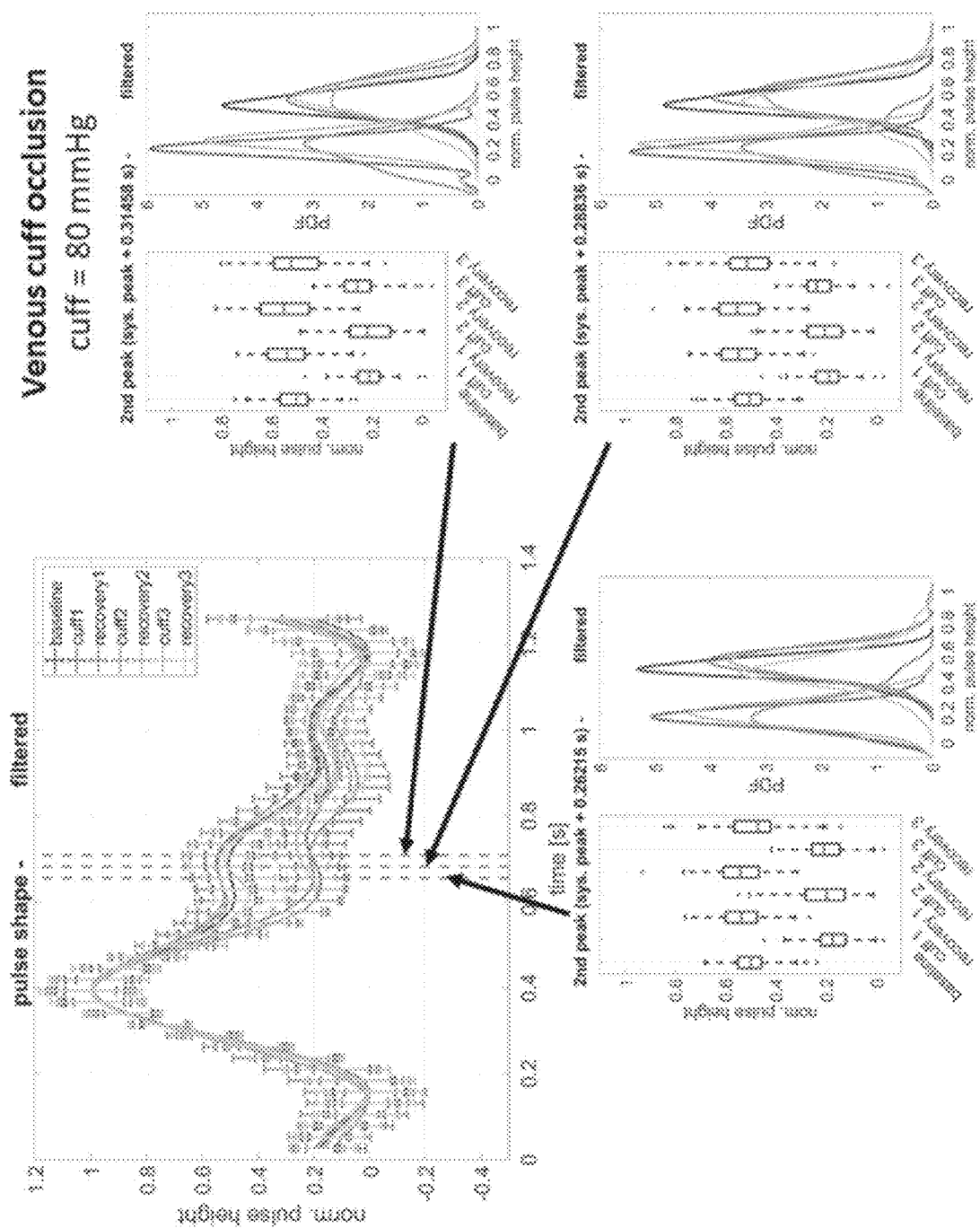
FIG. 8 shows an example of a venous cuff occlusion experiment. The pulse shape changes with applied pressure.

FIG. 8 shows an example of a venous cuff occlusion experiment in order to demonstrate changes of the pulse contour due to external influences. In preliminary tests, a venous cuff occlusion was applied on the forearm to volunteer subjects to simulate the effect of slightly increased pressure on the vessels, as in the case of hypertension in the brain or in the legs and arms. After a baseline of 3 minutes, the arm was cuffed with a pressure of 80 mmHg. After two minutes with the applied cuff pressure, the cuff was released, after which there was a recovery phase of 2 minutes. The venous cuff occlusion and the recovery was repeated three times in total. Concretely, the phases of the experiment were: baseline, first cuff occlusion (cuff 1), first recovery (recovery 1), second cuff occlusion (cuff 2), second recovery (recovery 2), third cuff occlusion (cuff 3), third recovery (recovery 3). Additionally, there was a wrist cuff (cuffed above the systolic pressure) applied during the entire measurement in order to get rid of the circulation of the hand which might influence the results.

Pulsatile blood flow was calculated from the acquired fastDCS signal (autocorrelation curves) and the signal was split into the aforementioned phases. In each phase, the systolic peaks 112 were detected and based on that the pulses were averaged for each phase. The pulse height was normalized from zero to one for the systolic peak 112, allowing the height and the shape of the diastolic contribution to be compared. FIG. 8 shows the results of the performed measurements. The diastole shows a clear decrease in amplitude during the cuff occlusion phases (cuff 1, cuff 2, cuff 3)

compared to the baseline and the recovery phases (recovery 1, recovery 2, recovery 3). Furthermore, three consecutive points of the second peak 122 were analyzed in more detail. FIG. 8 shows boxplots of the heights at the second peak 122 of the detected peaks and their probability distribution functions in each phase. The group of the cuffed phases shows a change in normalized pulse height in all three points. It is thus obvious that the shape of the pulse changed due to cuff occlusion.

Figure 9:
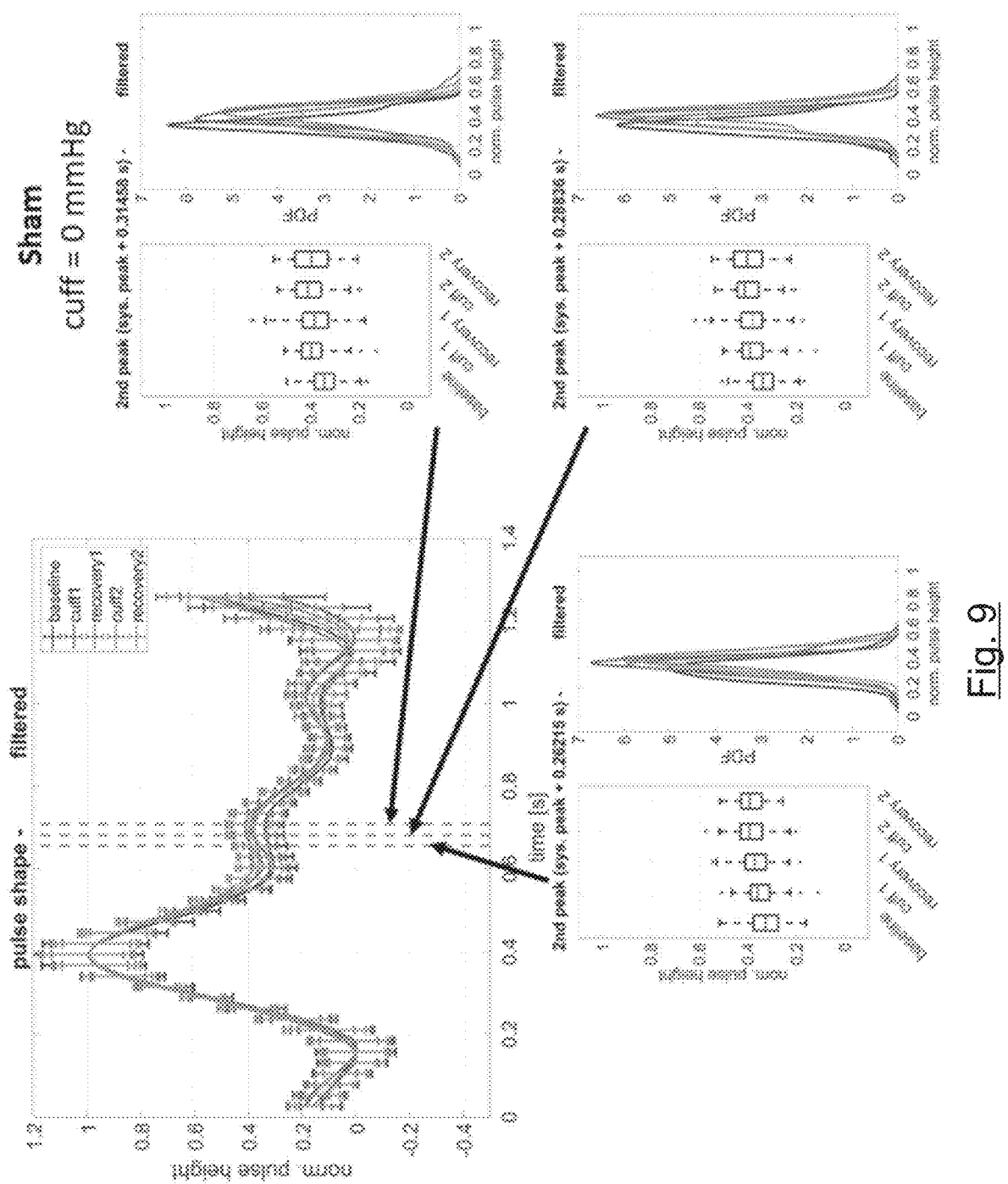
FIG. 9 shows an example of a sham measurement of venous cuff occlusion. The pulse shape does not change due to external influences.

In comparison, FIG. 9 shows the results of a sham measurement where the cuff was not inflated and no challenge was applied. There were no obvious changes between the different phases.

This preliminary experiment shows the practical potential of the method and system in the present invention to detect and categorize a pathology (in this example, pressure changes) based on the analysis of the pulse shape of the pulsatile blood flow. The goal of the method is not to measure absolute values, but rather to derive an index which may or may not correspond to the absolute values.

Figure 10A:
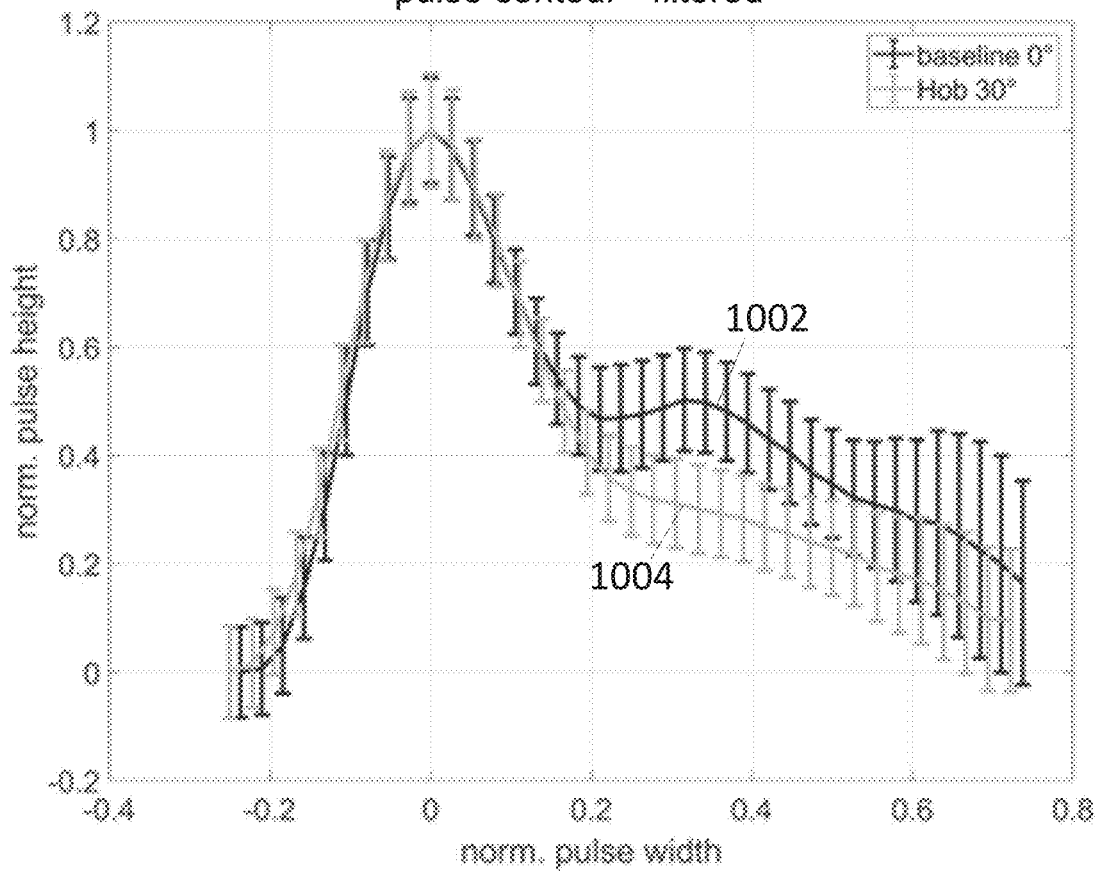
FIG. 10A depicts the results of the pulse shape analysis of a head-of-bed measurement.
Figure 10A:
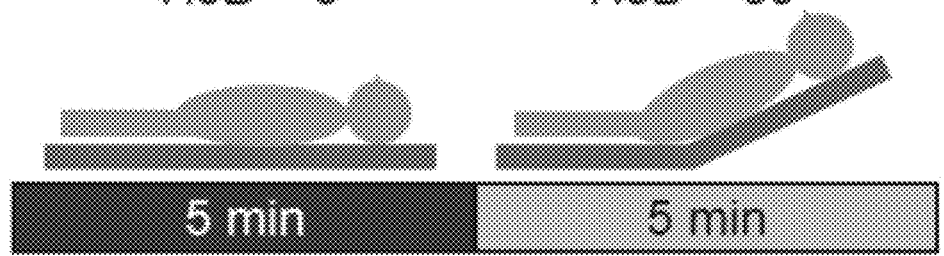
Figure 10B:
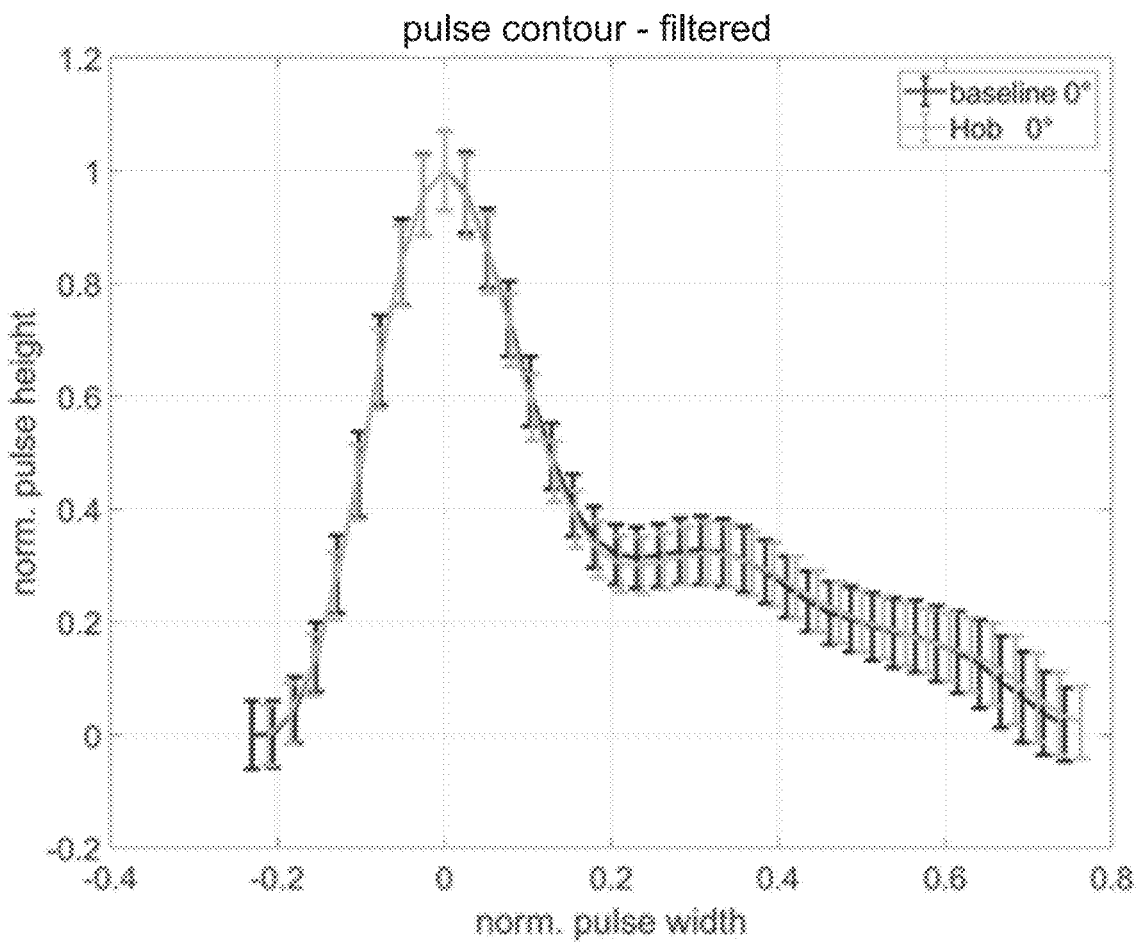
FIG. 10B depicts the results of the pulse shape analysis compared to a sham measurement.
Figure 10B:
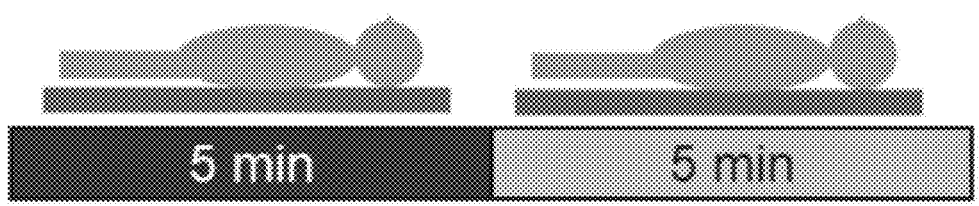

FIGS. 10A and 10B show results obtained on further experiments conducted on a subject. The tests were performed on the head, for different angles of head-of-bed elevation. A probe was applied on the forehead of a subject in order to measure the blood flow in the frontal lobe of the brain. In the first experiment, FIG. 10A, the subject was in supine position (head-of-bed (HoB) angle=0°) for a baseline measurement of 5 minutes. After the baseline, the bed was inclined to a HoB angle of 30° for another 5 minutes, during which data from the probe was acquired. In the inclined position, a lower ICP is expected according to literature (e.g. Feldman et al., "Effect of head elevation on intracranial pressure, cerebral perfusion pressure, and cerebral blood flow in head—injured patients", J Neurosurg 76, 1992). Pulsatile blood flow was again calculated from the acquired fastDCS signal and the same procedure applied to average the pulses of each phase. The averaged pulse was normalized in height and width.

FIG. 10A shows the normalized average pulse shape for both phases (HoB=0°; HoB=30°). The second peak 122 of the waveform of the second phase 1004 (HoB=30°) clearly changed with respect to the shape of the waveform of the baseline 1002. In comparison, a second experiment was also conducted, a sham measurement where the HoB angle was kept 0° also for the second 5 minutes of the measurement. The obtained result is shown in FIG. 10B. It is evident that the pulse shape did not change in the case of the sham measurement. These measurements shown in FIGS. 10A and 10B demonstrate as a proof-of-principle that a change of HoB angle can be detected by obtaining pulsatile blood flow on the head of a subject and analyzing changes in the pulse shape.

Figure 11:
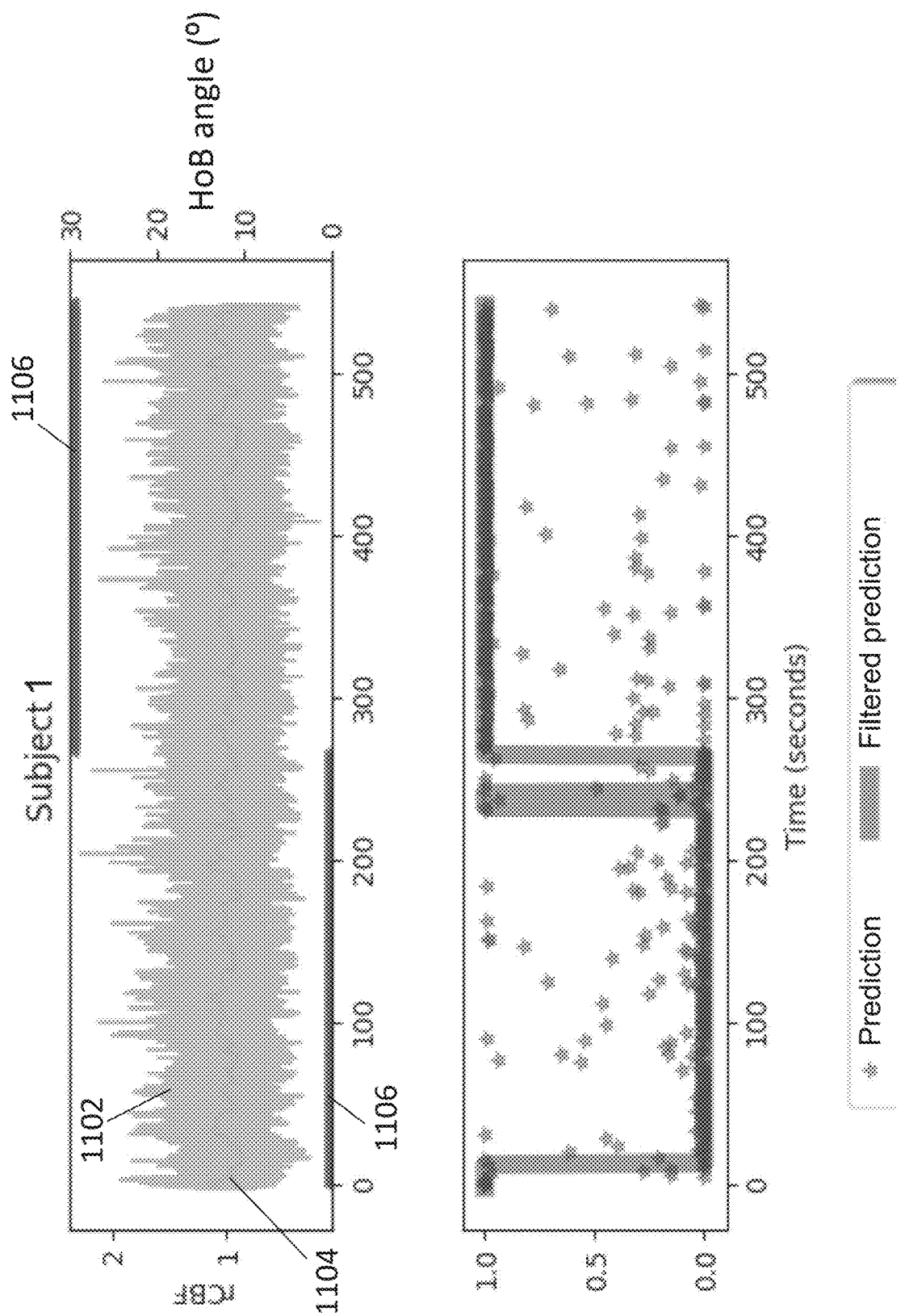
FIG. 11 shows example data for a first subject, including pulsatile blood flow signal (upper graph) and the predicted head of bed position (lower graph).
Figure 12:
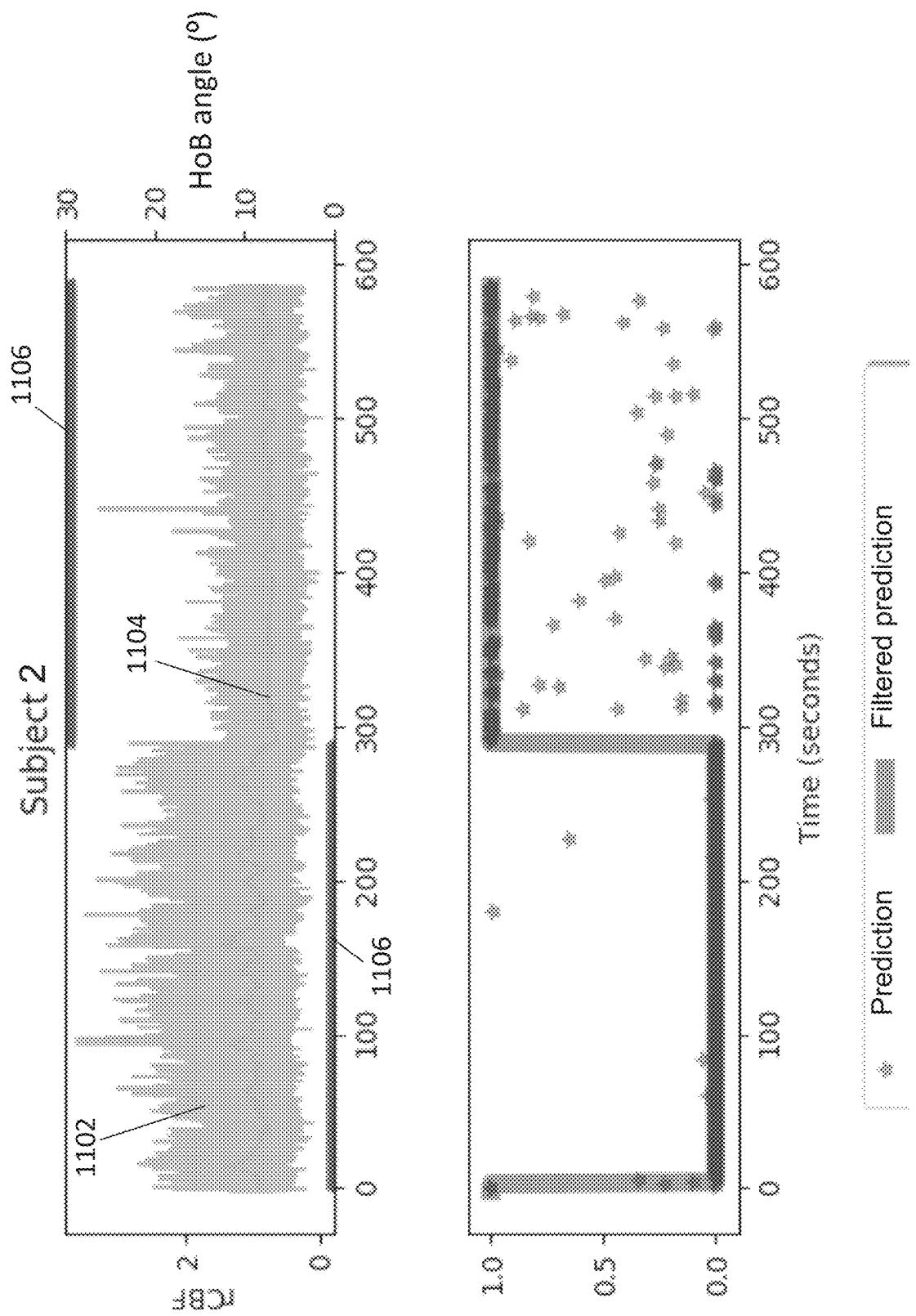
FIG. 12 shows example data for a second subject, including pulsatile blood flow signal (upper graph) and the predicted head of bed position (lower graph).
Figure 13:
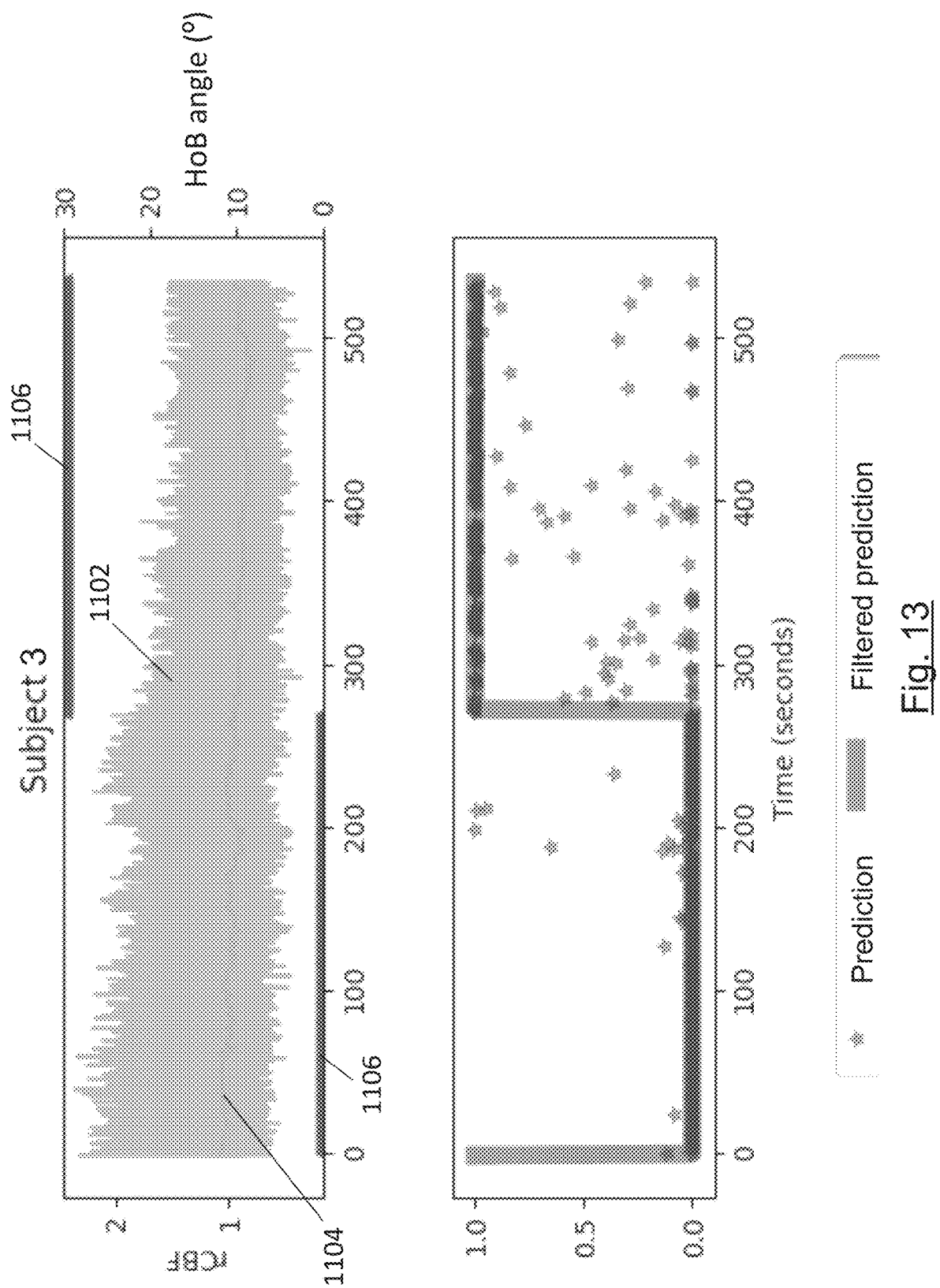
FIG. 13 shows example data for a third subject, including pulsatile blood flow signal (upper graph) and the predicted head of bed position (lower graph).
Figure 14:
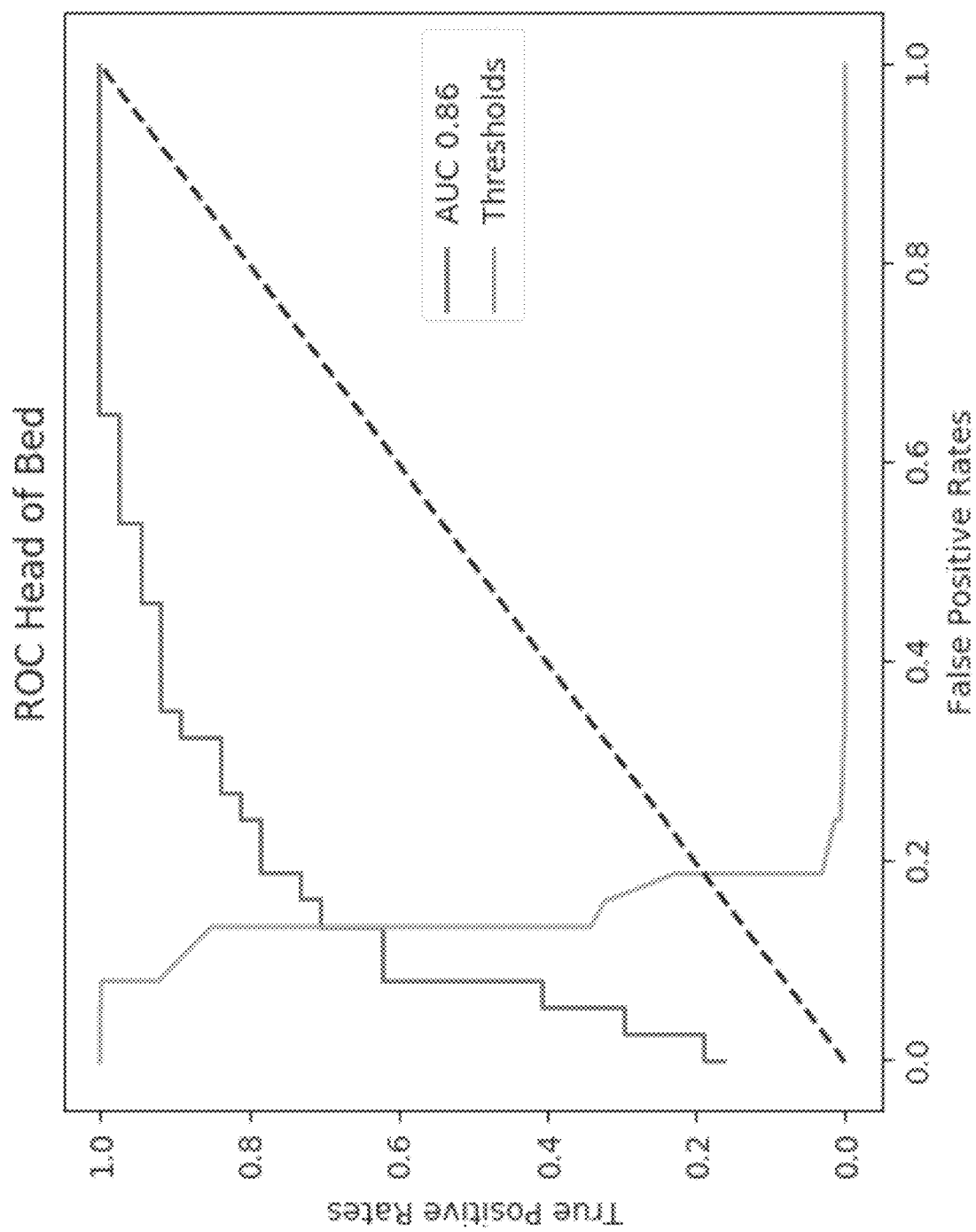
FIG. 14 depicts the ROC for classification of HoB position predictions of the small data set with ten subjects.

In total ten healthy subjects and five healthy shams have been recruited and measured with the HoB protocol and the described algorithm was used for determining the head of bed position of healthy subjects given the pulsatile blood flow signal. FIGS. 11, 12 and 13 show in the upper graph the data acquired (pulsatile blood flow signal 1102 and mean blood flow value 1104 for two different head-of-bead positions 1106 –0° and 30°–) and in the lower graph the predicted head-of-bed position for three different subjects. These figures show that the pulsatile blood flow signal 1102 is sensitive to HoB positional change, independent of the mean blood flow value 1104. From the ROC plot in FIG. 14, an inflection point can be seen on the predictor for 30 degree HoB position at 20% false positive rate and 75% true positive rate, providing a reasonably fair assessor of a HoB class. Furthermore, an area under the curve (AUC) of 0.86 was determined, which further attests to the predictors promise in performing well in terms of sensitivity and specificity. Such distinctions will need to be tuned (i.e. what is an acceptable true positive and true negative rate) per different applications as needed.

Figure 15A:
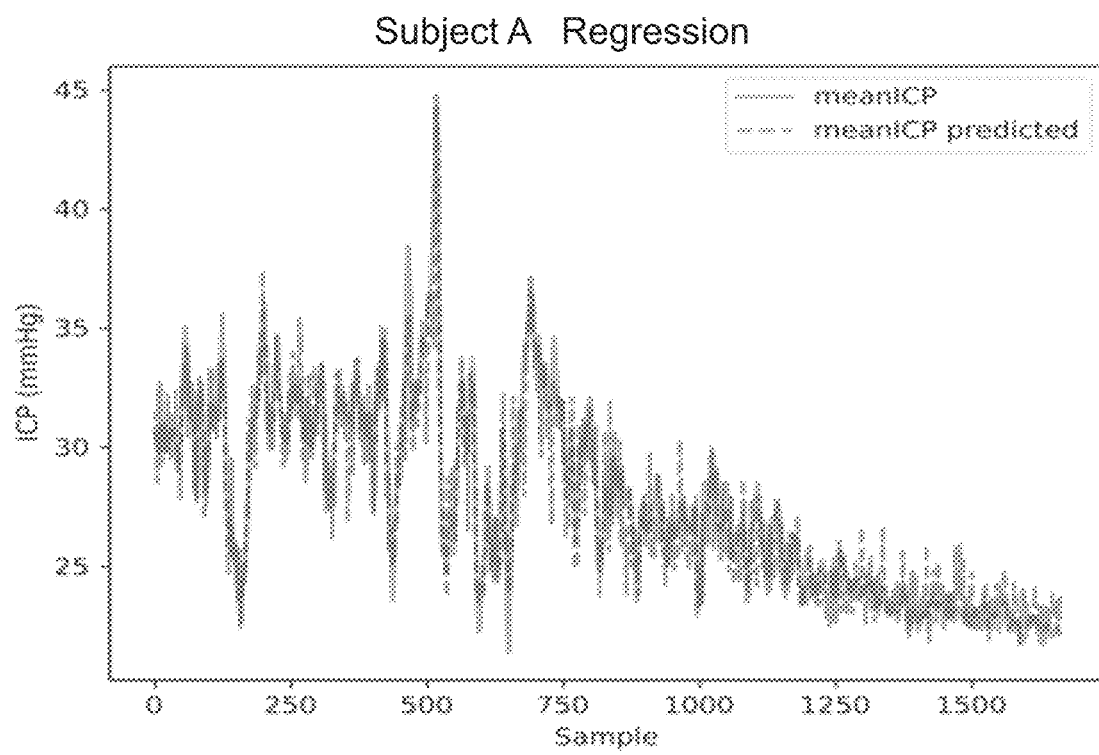
FIG. 15A depicts the regression of time windows of pulsatile blood flow with mean ICP value of subject A.
Figure 15B:
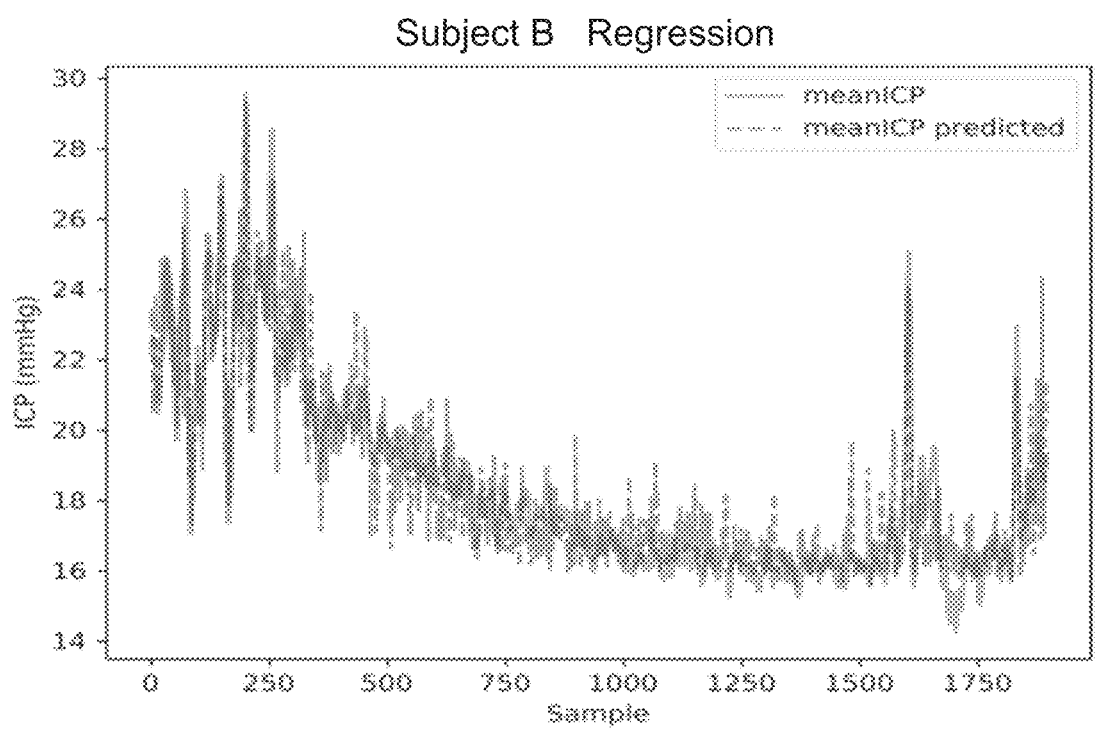
FIG. 15B depicts the regression of time windows of pulsatile blood flow with mean ICP value of subject B.
Figure 16A:
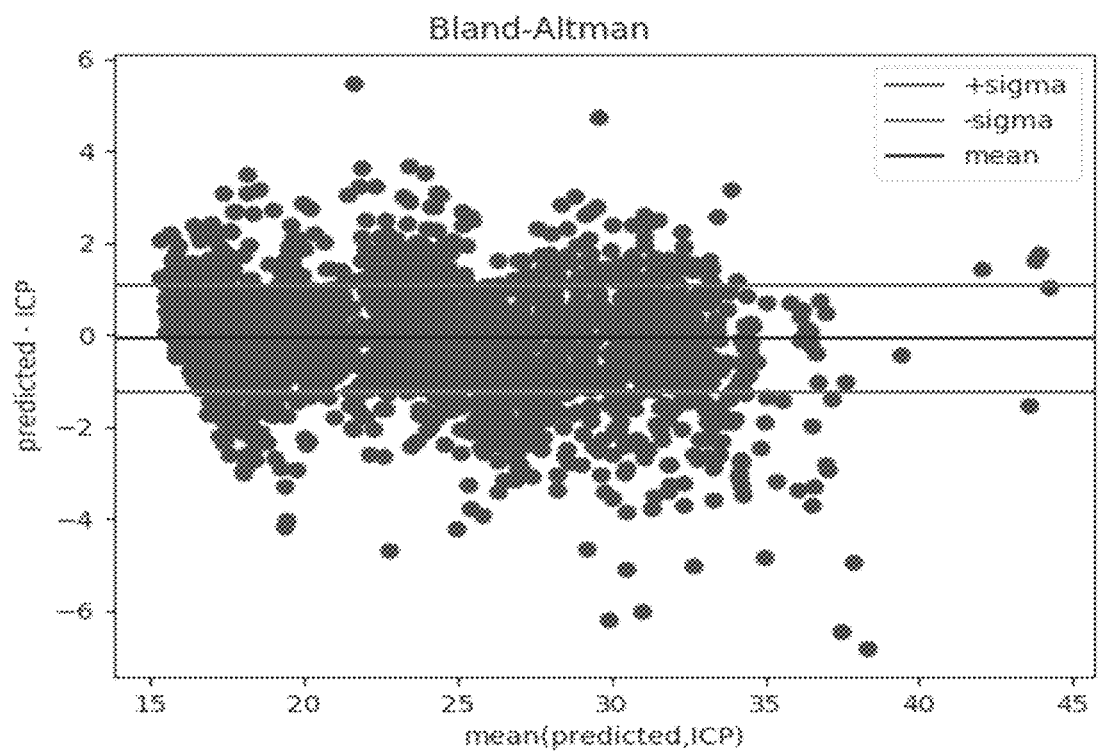
FIG. 16A depicts a correlation between the predicted values of ICP with the real value of ICP alongside a Bland-Altman plot.
Figure 16B:
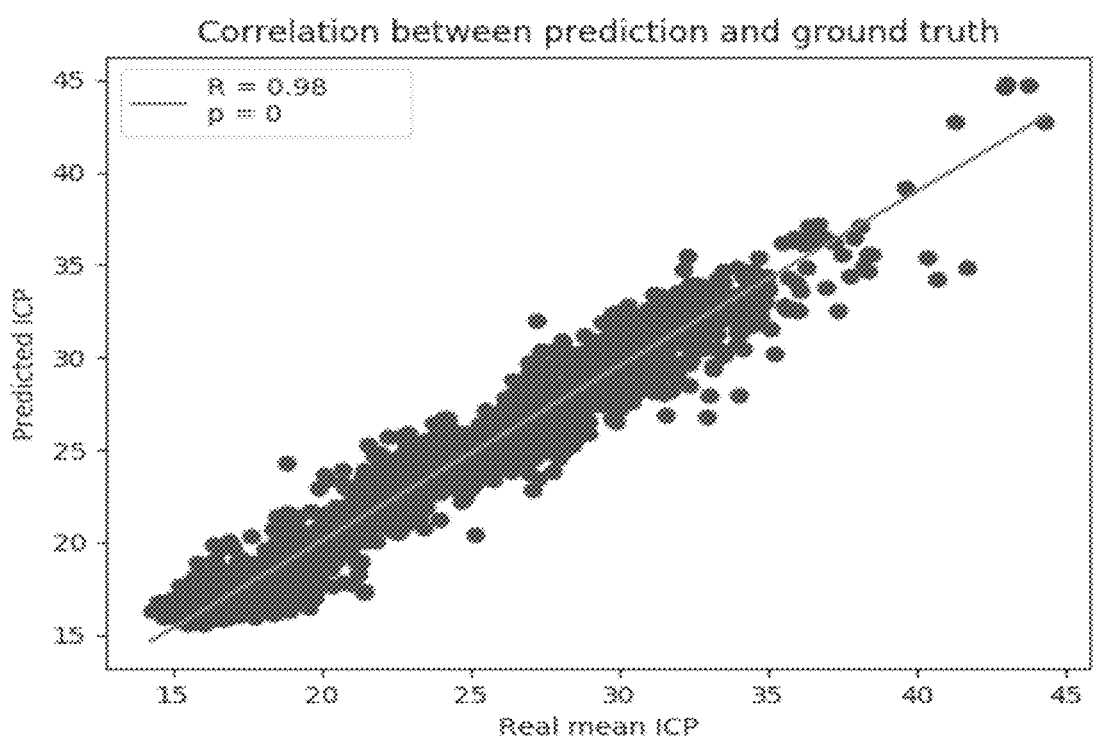
FIG. 16B describes the level of agreement over a range of measurements that the predicted ICP value has with mean ICP.

In FIGS. 15 and 16, the present method demonstrates further potential to be used in the demonstrated application of ICP, as shown in the embodiment in FIG. 3. In a study with infants with an age of 1 month to 42 months suffering from external benign hydrocephalus, two subjects (subject A and subject B) with an invasive ICP sensor have been recruited to measure with fastDCS alongside the normal ICP monitoring as a preliminary demonstration. From the direct regressions demonstrated in FIGS. 15A and 15B, it can be seen that for the two subjects with entirely different ranges of ICP values, a direct value was able to be determined. Furthermore, in FIG. 16A, a Bland-Altman plot shows that within a deviation of 2 mmHg, the regression was able to predict the real ICP value. In FIG. 16B, a correlation of R=0.98 was found, showing that there is a near 1:1 ratio between the prediction learned and the real value, i.e. they report the same results. These regressions show promise considering that, as mentioned before and demonstrated in FIG. 16A, an agreement with deviation as small as 2 mmHg allows the potential for the objective for indices of ICP to be realized. For example, determining a high confidence interval in a range of normal, moderate, and severe with high sensitivity and specificity can be realized with such types of results. Furthermore, such high correlation and agreement of the predicted ICP and the real ICP could allow one to create a continuous normalized index that can be used to determine a severity of ICP.

The invention claimed is:

1. A computer-implemented method for detecting and categorizing pathologies of the brain causing altered pulsatile blood flow, comprising:
    acquiring a pulsatile blood flow signal of the brain of a subject by an optical device implementing optical techniques based on laser speckle statistics, wherein the pulsatile blood flow signal is a time series of pulsatile blood flow data points comprising at least one cardiac cycle; and
    determining a severity of a pathology of the brain causing altered pulsatile blood flow by applying as input to a processor implementing a machine learning algorithm data representative of the time series of the pulsatile blood flow data points comprising at least one cardiac cycle, and using said machine learning algorithm to process said inputted data:
        to learn relevant features from the pulse contour or from previously extracted/pre-processed features of the pulse contour, of the time series of the pulsatile blood flow data points, and
        to assess the set of learned features to categorize the set of learned features into different classes or build an index or score of affected physiology,
    wherein the machine learning algorithm is trained with pulsatile blood flow pulse contour measurements.

2. The computer-implemented method of claim 1, wherein the extracted features are selected from the group consisting of:
    systolic amplitude;
    diastolic amplitude;
    systolic to diastolic amplitude ratio;
    systole to diastole time difference of the same pulse;
    diastole of one pulse to the systole of the next pulse;

systole full width half maximum (FWHM);
diastole FWHM;
slope of the diastole decline;
slope of the systole decline;
standard deviation of the systole;
standard deviation of the diastole; and
a combination thereof.

3. The computer-implemented method of claim 1, wherein the extracted features are obtained via a time-frequency analysis.

4. The computer-implemented method of claim 1, further comprising receiving a plurality of static features of the subject, wherein the pathology is categorized based on both the extracted features and the static features.

5. The computer-implemented method of claim 1, further comprising displaying the result of the categorization on a display.

6. A system for detecting and categorizing pathologies of the brain causing altered pulsatile blood flow, the system comprising:
   an optical device configured to acquire a pulsatile blood flow signal of the brain of a subject, and that implements optical techniques based on laser speckle statistics, wherein the pulsatile blood flow signal is a time series of pulsatile blood flow data points comprising at least one cardiac cycle; and
   a processing device including:
      a preprocessing module operatively connected to the optical device to receive the acquired pulsatile blood flow signal therefrom and configured to preprocess that acquired pulsatile blood flow signal; and
      a machine learning algorithm processor implementing a machine learning algorithm, operatively connected to the preprocessing module to receive a preprocessed pulsatile blood flow signal therefrom, and configured to determine a severity of a pathology of the brain causing altered pulsatile blood flow by processing data representative of the time series of the pulsatile blood flow data points of the preprocessed pulsatile blood flow signal:
         to learn relevant features from the pulse contour or from previously extracted/pre-processed features of the pulse contour, of the time series of the pulsatile blood flow data points, and
         to assess the set of learned features to categorize the set of learned features into different classes or build an index or score of affected physiology;
      wherein the machine learning algorithm is trained with pulsatile blood flow pulse contour measurements.

7. The system of claim 6, wherein said optical device is a diffuse correlation spectroscopy device configured to acquire the pulsatile blood flow signal of the brain of the subject, said optical device comprising a plurality of optical sources, a plurality of optical detectors and a correlator.

8. A non-transitory computer-readable storage medium for detecting and categorizing pathologies of the brain causing altered pulsatile blood flow, comprising computer code instructions that, when executed by a processor, causes the processor to perform the method of claim 1.

* * * * *